United States Patent
Yi et al.

(10) Patent No.: US 9,747,703 B2
(45) Date of Patent: Aug. 29, 2017

(54) X-RAY IMAGING APPARATUS AND METHOD OF CONTROLLING THE SAME

(71) Applicant: SAMSUNG ELECTRONICS CO., LTD., Suwon-si (KR)

(72) Inventors: Jaemock Yi, Hwaseong (KR); Young Hun Sung, Hwaseong (KR); Jae Hak Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 103 days.

(21) Appl. No.: 14/729,604

(22) Filed: Jun. 3, 2015

(65) Prior Publication Data

US 2015/0348290 A1    Dec. 3, 2015

(30) Foreign Application Priority Data

Jun. 3, 2014    (KR) .................. 10-2014-0067915

(51) Int. Cl.
*H05G 1/64* (2006.01)
*G06T 11/00* (2006.01)
*A61B 6/00* (2006.01)
*G06T 3/40* (2006.01)

(52) U.S. Cl.
CPC .......... *G06T 11/005* (2013.01); *A61B 6/4233* (2013.01); *A61B 6/4441* (2013.01); *A61B 6/461* (2013.01); *A61B 6/504* (2013.01); *A61B 6/5205* (2013.01); *G06T 3/4053* (2013.01); *G06T 11/006* (2013.01)

(58) Field of Classification Search
CPC ...... G06T 11/00; G06T 11/003; G06T 11/005; G06T 11/008; A61B 6/4233
USPC ................ 378/91, 92, 98, 114, 115, 116
See application file for complete search history.

(56) References Cited

U.S. PATENT DOCUMENTS

| | | | |
|---|---|---|---|
| 4,908,573 A * | 3/1990 | Kaufman | G01R 33/4822 324/309 |
| 2003/0169850 A1* | 9/2003 | Kump | A61B 6/405 378/207 |
| 2009/0218476 A1* | 9/2009 | Kameshima | A61B 6/00 250/208.1 |
| 2013/0163716 A1* | 6/2013 | Okada | G01T 1/16 378/19 |
| 2013/0336451 A1* | 12/2013 | Nishii | G01N 23/00 378/62 |

* cited by examiner

*Primary Examiner* — Jason McCormack
(74) *Attorney, Agent, or Firm* — Sughrue Mion, PLLC

(57) ABSTRACT

An X-ray imaging apparatus includes an X-ray detector including pixels, which is configured to change a pattern of binning applied to pixels and obtain first resolution X-ray images; and an image processor configured to reconstruct a second resolution X-ray image using the first resolution X-ray images.

20 Claims, 35 Drawing Sheets

READOUT PATTERN OF X-RAY DETECTOR

RESOLUTION OF OUTPUT IMAGE

READOUT PATTERN OF X-RAY DETECTOR    RESOLUTION OF OUTPUT IMAGE

SECOND IMAGING

FOURTH IMAGING

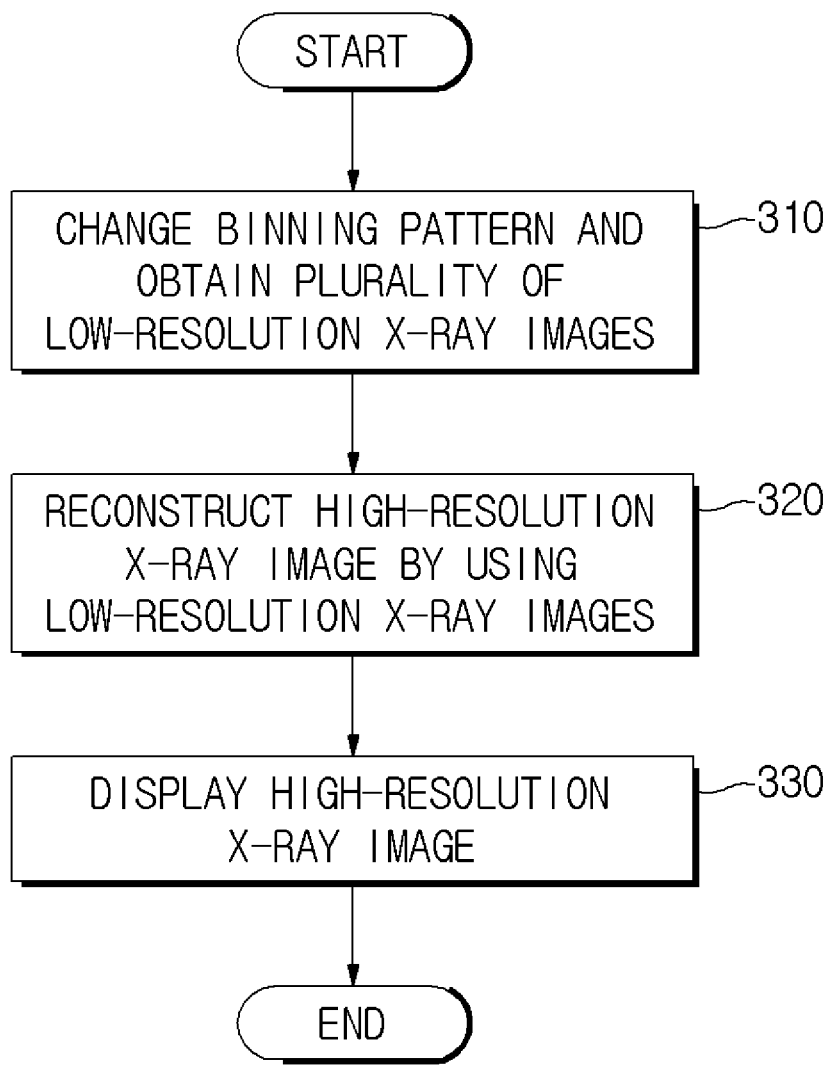

X-RAY IMAGING APPARATUS AND METHOD OF CONTROLLING THE SAME

CROSS-REFERENCE TO RELATED APPLICATION

This application claims priority from Korean Patent Application No. 10-2014-0067915, filed on Jun. 3, 2014 in the Korean Intellectual Property Office, the disclosure of which is incorporated herein by reference in its entirety.

BACKGROUND

1. Field

Apparatus and methods consistent with exemplary embodiments relate to an X-ray imaging apparatus configured to transmit X-rays onto an object and image an internal region of the object and a method of controlling the same.

2. Description of the Related Art

An X-ray imaging apparatus is an apparatus capable of obtaining an internal image of an object by transmitting X-rays onto the object and using X-rays having penetrated through the object. Since permeability of X-rays differs depending on properties of a material included in the object, it is possible to image an internal structure of the object using an intensity or a strength of X-rays having penetrated through the object.

Recently, to increase a resolution of an X-ray image, the number of pixels forming an X-ray detector has been increasing. However, when the number of pixels increases, a noise characteristic is degraded and a large number of X-ray photons are needed to obtain an image. That is, an amount of X-ray exposure of the object increases.

Therefore, to improve the noise characteristic of the X-ray image, a pixel binning technique in which signals generated from a plurality of pixels are grouped and read as one signal may be used. When pixel binning is applied, the noise characteristic of the X-ray image is improved. However, it is difficult to obtain a high-resolution X-ray image by using a high-resolution X-ray detector when the pixel binning technique is applied.

SUMMARY

One or more exemplary embodiments provide an X-ray imaging apparatus, which is capable of obtaining an excellent noise characteristic and an excellent resolution at the same time by applying pixel binning and reconstructing a high-resolution X-ray image from a low-resolution X-ray image, and a method of controlling the same.

According to an aspect of an exemplary embodiment, there is provided an X-ray imaging apparatus, including: an X-ray detector configured to change a binning pattern applied to pixel binning and obtain a plurality of low-resolution X-ray images; and an image processor configured to reconstruct a high-resolution X-ray image using the plurality of obtained low-resolution X-ray images.

The X-ray detector may horizontally or vertically shift the binning pattern by at least one pixel size and change the binning pattern.

The X-ray detector may include: a plurality of pixels that are two dimensionally arranged and output signals corresponding to incident X-rays; a plurality of gate lines configured to connect the plurality of pixels in a row direction; a plurality of data lines configured to connect the plurality of pixels in a column direction; a readout circuit configured to obtain signals from the plurality of pixels through the plurality of data lines; and a switch configured to independently connect the plurality of data lines and the readout circuit for each of the data lines.

The switch may include a plurality of switches connected to the plurality of data lines, respectively.

At least one of the plurality of switches may be a two-way switch.

The two-way switch may selectively connect p (p is the number of columns included in one binning set) data lines among the plurality of data lines.

Signals obtained from the selectively connected p data lines may be combined as one signal and input to the readout circuit.

Groups of p (p is the number of data lines included in one binning set) of the plurality of switches may be turned on with a time difference.

The X-ray detector may include: a plurality of pixels that are two dimensionally arranged and output signals corresponding to incident X-rays; a plurality of gate lines configured to connect the plurality of pixels in a row direction; a plurality of data lines configured to connect the plurality of pixels in a column direction; and a readout circuit configured to obtain signals from the plurality of pixels through the plurality of data lines.

The readout circuit may include a multiplexer that outputs groups of p (p is the number of data lines included in one binning set) signals among signals obtained from the plurality of data lines with a time difference.

The X-ray imaging apparatus may further include p amplifiers connected to an output terminal of the multiplexer.

The X-ray detector may change the binning pattern and obtain the plurality of low-resolution X-ray images having different pieces of pixel information on the same scene.

The image processor may use at least one of a spatial domain method in which a relation between a low-resolution image and a high-resolution image is analyzed in a space domain and the high-resolution image is reconstructed and a frequency domain method in which a relation between a low-resolution image and a high-resolution image is analyzed in a frequency domain and the high-resolution image is reconstructed.

The X-ray imaging apparatus may further include an X-ray source configured to transmit X-rays that are detected by the X-ray detector.

The X-ray detector may obtain a video composed of a plurality of frame images, and the plurality of frame images may include the plurality of low-resolution X-ray images.

The image processor may reconstruct the high-resolution X-ray image whenever the frame image is input.

When a predetermined number of frame images are input, the image processor may reconstruct the high-resolution X-ray image using the predetermined number of frame images.

The X-ray imaging apparatus may further include a display configured to display the reconstructed high-resolution X-ray image.

According to an aspect of an exemplary embodiment, there is provided a method of controlling an X-ray imaging apparatus, including changing a binning pattern applied to pixel binning and obtaining a plurality of low-resolution X-ray images; and reconstructing a high-resolution X-ray image using the plurality of low-resolution X-ray images.

The changing of the binning pattern may include horizontally or vertically shifting the binning pattern by at least one pixel size.

In the obtaining of the plurality of low-resolution X-ray images, an X-ray detector may be used, the detector including: a plurality of pixels that are two dimensionally arranged and output electrical signals corresponding to incident X-rays; a plurality of gate lines configured to connect the plurality of pixels in a row direction; a plurality of data lines configured to connect the plurality of pixels in a column direction; and a readout circuit configured to obtain signals from the plurality of pixels through the plurality of data lines.

The obtaining of the plurality of low-resolution X-ray images may include selectively connecting p (p is the number of columns included in one binning set) data lines among the plurality of data lines, and combining signals obtained from the connected p data lines as one signal and inputting the result to the readout circuit.

The obtaining of the plurality of low-resolution X-ray images may include sequentially obtaining signals by combining the plurality of data lines in groups of p.

The obtaining of the plurality of low-resolution X-ray images may include outputting groups of p (p is the number of columns included in one binning set) signals among signals obtained from the plurality of data lines with a time difference.

The obtaining of the plurality of low-resolution X-ray images may include obtaining a video composed of a plurality of frame images.

The obtaining of the plurality of low-resolution X-ray images may include reconstructing the high-resolution X-ray image whenever the frame image is input.

In the obtaining of the plurality of low-resolution X-ray images, when a predetermined number of frame images are input, the high-resolution X-ray image may be reconstructed using the predetermined number of frame images.

The method may further include displaying the reconstructed high-resolution X-ray image.

In accordance with an aspect of an exemplary embodiment, there is provided an X-ray detector including: a two-dimensional (2D) array of pixels configured to output signals corresponding to incident X-rays; gate lines configured to connect the pixels in a first direction; data lines configured to connect the pixels in a second direction; a readout circuit configured to obtain signals from the pixels through the data lines, respectively; a switch configured to selectively connect the data lines to the readout circuit; and a detector controller configured to control the switch to change a pattern of binning applied to the pixels and obtain X-ray images.

BRIEF DESCRIPTION OF THE DRAWINGS

The above and/or other aspects will become more apparent by describing certain exemplary embodiments with reference to the accompanying drawings, in which:

FIG. 28 is a flowchart illustrating a method of controlling an X-ray imaging apparatus according to an exemplary embodiment.

DETAILED DESCRIPTION

Figure 1:
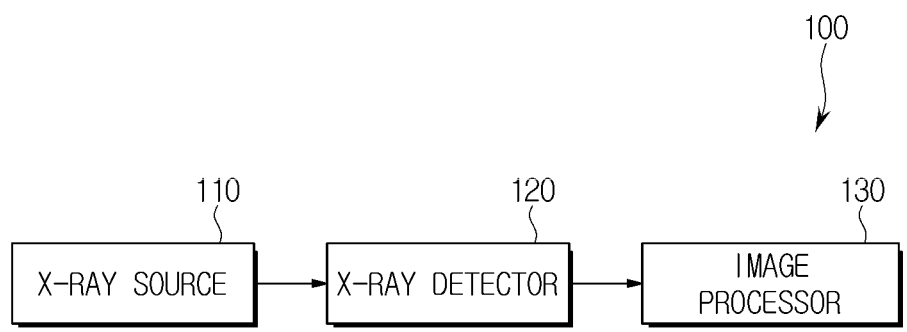
FIG. 1 is a control block diagram illustrating an X-ray imaging apparatus according to an exemplary embodiment.

Reference will now be made in detail to exemplary embodiments with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Figure 2:
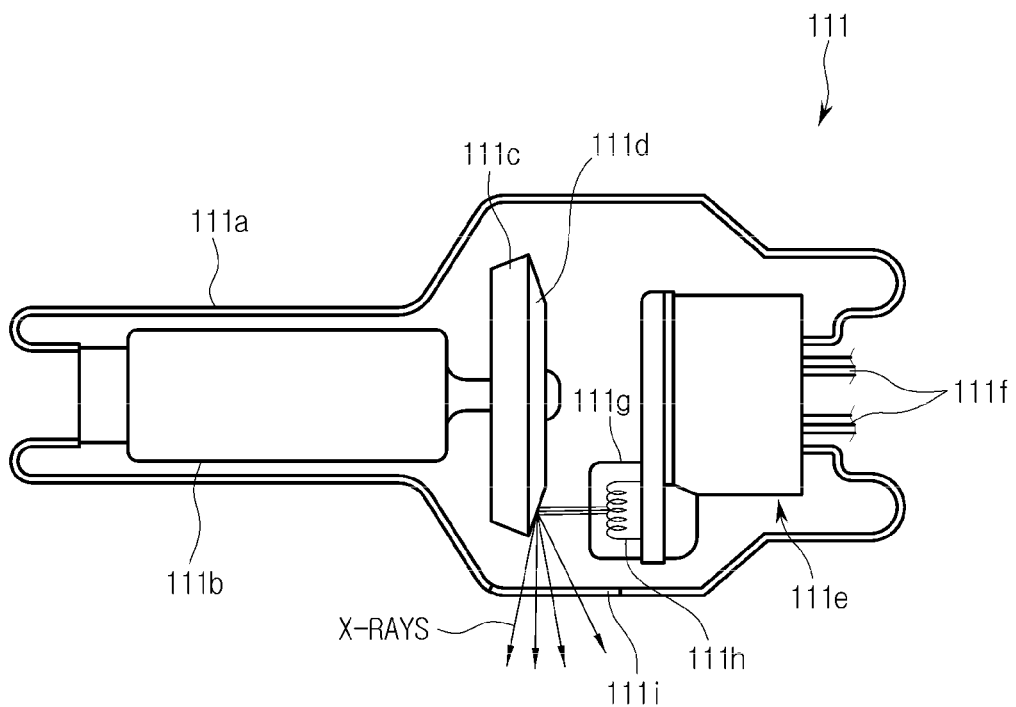
FIG. 2 is a view illustrating a configuration of an X-ray source.
Figure 3:
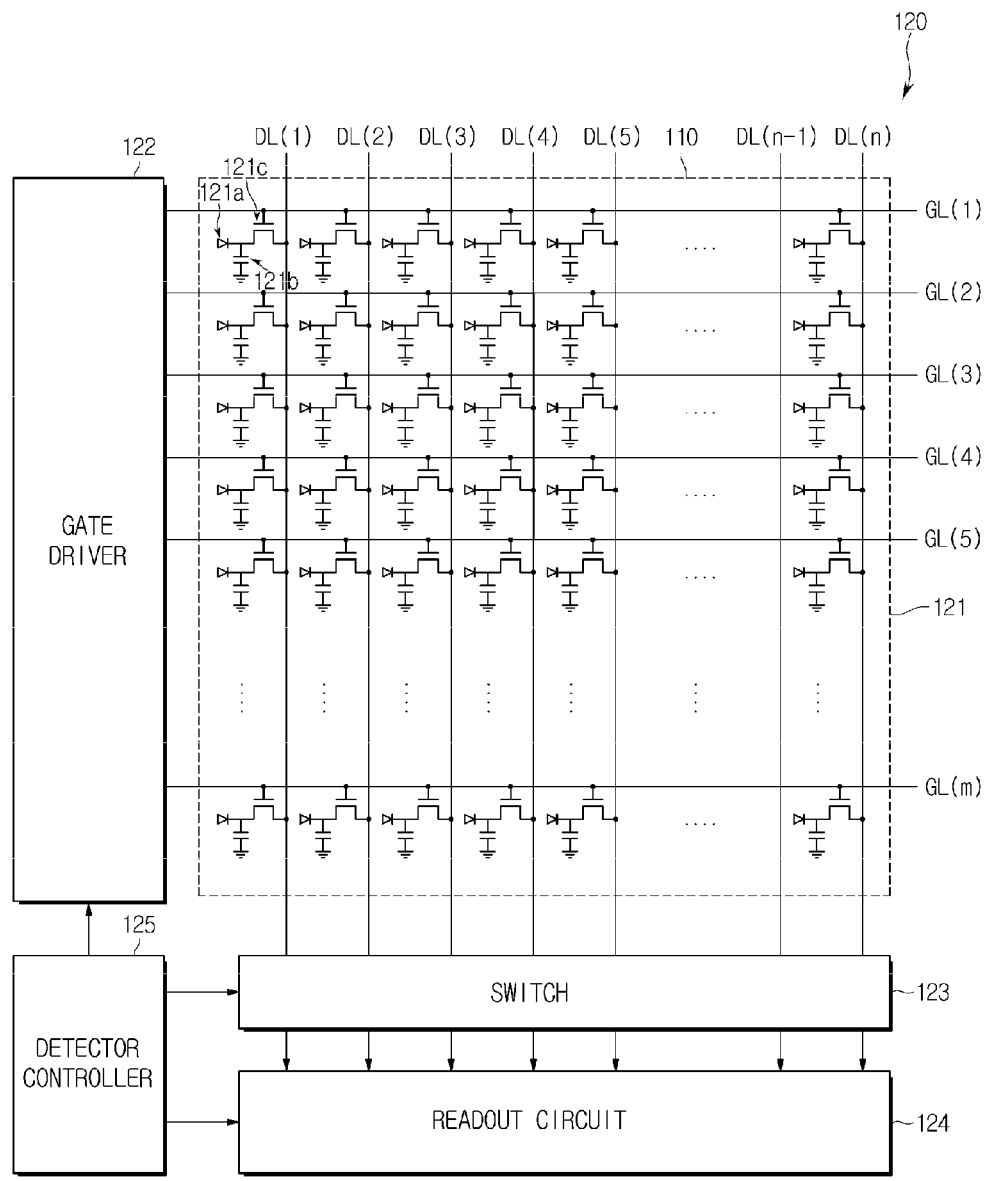
FIG. 3 is a diagram illustrating a structure of an X-ray detector.

FIG. 1 is a control block diagram illustrating an X-ray imaging apparatus according to an exemplary embodiment. FIG. 2 is a view illustrating a configuration of an X-ray source. FIG. 3 is a diagram illustrating a structure of an X-ray detector.

As illustrated in FIG. 1, an X-ray imaging apparatus 100 according to an exemplary embodiment includes an X-ray source 110 configured to generate and transmit X-rays, an X-ray detector 120 configured to detect X-rays having penetrated through an object and an image processor 130 configured to generate an X-ray image in which an internal region of the object is imaged using the detected X-rays.

The X-ray source 110 includes an X-ray tube configured to generate X-rays. As illustrated in FIG. 2, an anode 111b and a cathode 111e are provided inside a glass tube 111a of an X-ray tube 111. An inside of the glass tube 111a is maintained in a high vacuum state and a filament 111h of the cathode 111e is heated to generate thermoelectrons. The filament 111h may be heated by applying a current to an electrical conductor 111f connected to the filament 111h. The cathode 111e includes the filament 111h and a focusing electrode 111g configured to focus electrons. The focusing electrode 111g is also called a focusing cup.

Also, when a high voltage is applied between the anode 111b and the cathode 111e, thermoelectrons are accelerated and collide with a target material 111d of the anode 111b and thereby X-rays are generated. A high-resistance material such as Cr, Fe, Co, Ni, W, or Mo may be used as the target material 111d of the anode 111b. The generated X-rays are transmitted to the outside through a window 111i and a beryllium (Be) film may be used as a material of the window 111i.

The voltage applied between the anode 111b and the cathode 111e is referred to as a tube voltage, and a level thereof may be indicated as peak kilovoltage (kvp). As the tube voltage increases, speeds of thermoelectrons increase. As a result, energy (or photon energy) generated by the X-rays colliding with the target material 111d increases. In addition, when a filter is disposed in a direction in which X-rays are transmitted, energy of X-rays may be adjusted. When a filter configured to filter X-rays of a specific wavelength band is positioned in front of or behind the window 111i, X-rays of a specific energy band may be filtered. For example, when a filter including aluminum or copper is disposed, X-rays of a low energy band are filtered and energy of transmitted X-rays increases.

A current flowing in the X-ray tube 111 is referred to as a tube current and may be indicated as an average current (mA). As the tube current increases, an X-ray dose (or the number of X-ray photons) increases. Therefore, energy of X-rays may be controlled by the tube voltage, and the X-ray dose may be controlled by the tube current and an X-ray exposure time.

As illustrated in FIG. 3, the X-ray detector 120 may include a detection area 121 that is an area in which X-rays are detected and the detected X-rays are converted into an electrical signal, a gate driver 122 configured to transmit a driving signal to the detection area 121, a readout circuit 124 configured to readout an electrical signal corresponding to an intensity of X-rays from the detection area 121, a switch 123 configured to connect the detection area 121 and the readout circuit 124, and a detector controller 125 configured to control the gate driver 122, the switch 123, and the readout circuit 124.

In addition, although not illustrated, an analog-to-digital converter (ADC) may be provided at an output terminal of the X-ray detector 120, and may convert an analog signal output from the readout circuit 124 into a digital signal and deliver the converted digital signal to the image processor 130.

A method of converting X-rays detected in the detection area 121 into an electrical signal includes a direct conversion method and an indirect conversion method.

In the direct conversion method, when X-rays are incident on the detection area 121, electron-hole pairs are temporarily generated inside a light-receiving element included in the detection area 121, electrons move to the anode 111b and holes move to the cathode 111e due to an electric field applied to both ends of the light-receiving element, and the readout circuit 124 readouts a flow of the electrons or the holes as an electrical signal. In the direct conversion method, a photoconductor such as amorphous selenium (a-Se), CdZnTe, HgI$_2$, or PbI$_2$ may be used as the light-receiving element.

In the indirect conversion method, the detection area 121 further includes a scintillator. When the incident X-rays react with the scintillator and are converted into visible light, the light-receiving element detects the converted visible light and converts the visible light into an electrical signal. In the indirect conversion method, a photodiode such as amorphous silicon (a-Si) may be used as the light-receiving element. A thin-film GADOX scintillator or a micro columnar or needle-shaped CSI (T1) scintillator may be used as the scintillator.

In the X-ray imaging apparatus 100 according to an exemplary embodiment, any of the direct conversion method and the indirect conversion method may be used. However, for illustrative purposes, an application of the indirect conversion method will be described below.

The detection area 121 includes pixels that are two-dimensionally arranged in an m×n matrix. Each pixel includes a photodiode 121a in which electric charges corresponding to an intensity of incident X-rays are generated, a capacitor 121b configured to store the generated electric charges, and a transistor 121c configured to turn on and/or off a flow of electric charges stored in the capacitor 121b along data lines DL(1), DL(2), . . . , DL(n) (collectively referred to as "DL").

As an example of the transistor 121c, a thin film transistor (TFT) may be used. However, the transistor 121c is only an example of a switching element. A switching element other than the transistor 121c may also be used.

The X-rays incident on the X-ray detector 120 are converted into visible light by the scintillator (not illustrated). When the converted visible light reaches the photodiode 121a, the photodiode 121a generates electric charges having an amount corresponding to an intensity of visible light. The generated electric charges are stored in the capacitor 121b.

When an ON signal is input to the transistor 121c, electric charges stored in the capacitor 121b flow along the data line DL. When the ON signal is not input, the transistor 121c maintains an off state and electric charges are accumulated in the capacitor 121b.

When a voltage signal of a predetermined level or higher is applied to a gate of the transistor 121c, electric charges stored in the capacitor 121b flow from a source to a drain of the transistor 121c. The voltage signal applied to the gate to turn on the transistor 121c is referred to as an ON signal or a gate signal.

The transistors 121c are connected to one of gate lines GL(1), GL(2), . . . , GL(m) (collectively referred to as "GL") for each row of the pixels and are connected to the data line DL for each column of the pixels. In an example of FIG. 3, n transistors 121c arranged in the same row are connected to a single gate line GL, and m transistors 121c arranged in the same column are connected to a single data line DL.

The gate driver 122 sequentially applies the gate signal to m gate lines GL(1), GL(2), ..., and GL(m). When the gate driver 122 applies the gate signal, that is, the ON signal, to the gate line GL, n transistors 121c connected to a corresponding gate line are turned on, and electric charges stored in the capacitor 121b of a corresponding pixel flow to the data line DL through the transistor 121c. That is, the X-ray detector 120 may obtain an X-ray image through a line scan.

To increase a noise characteristic of an image, an image obtaining rate, or a frame rate at which the X-ray image is obtained, the X-ray detector 120 may perform pixel binning and obtain a low-resolution X-ray image. In this case, a binning pattern is not fixed but is switched or changed, and a plurality of low-resolution X-ray images may be obtained. A structure and an operation of the X-ray detector 120 for performing the binning will be described below.

The image processor 130 may use the plurality of low-resolution X-ray images obtained by the X-ray detector 120 and reconstruct a high-resolution X-ray image. Description thereof will be described below.

Figure 4:
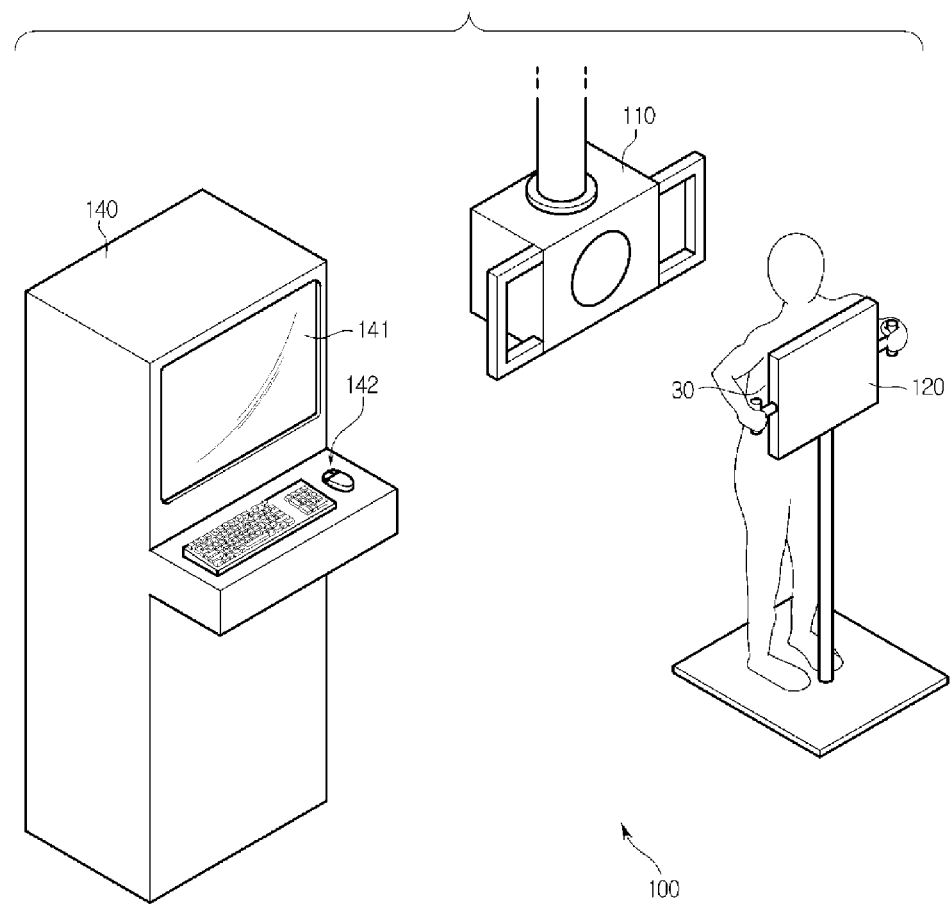
FIG. 4 is a diagram illustrating an X-ray imaging apparatus for performing radiography in an X-ray imaging apparatus according to an exemplary embodiment.
Figure 5:
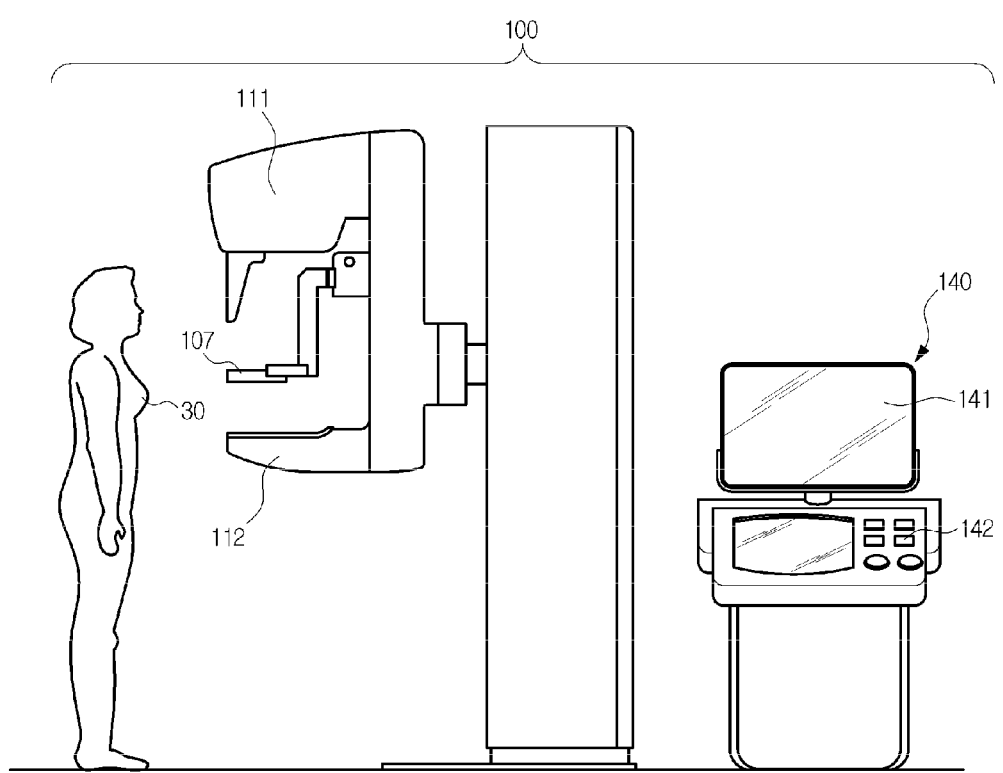
FIG. 5 is a diagram illustrating an X-ray imaging apparatus for performing mammography in an X-ray imaging apparatus according to an exemplary embodiment.
Figure 6:
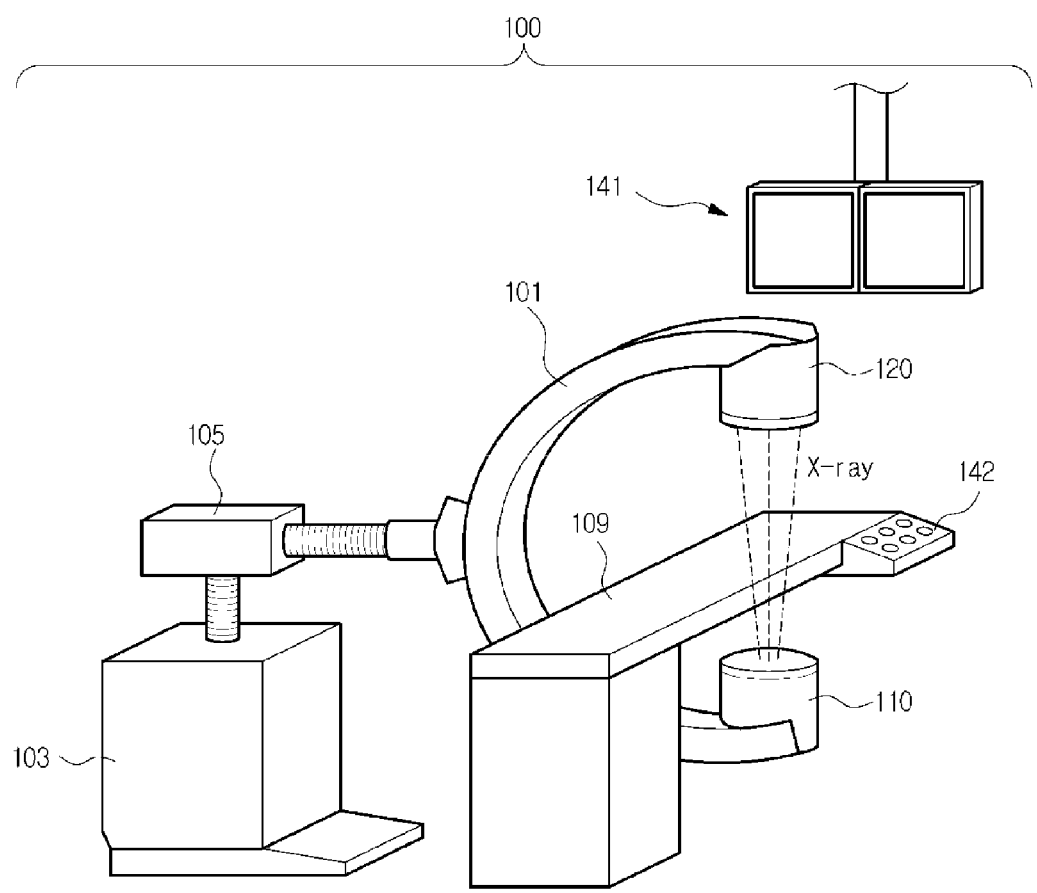
FIG. 6 is a diagram illustrating an X-ray imaging apparatus for imaging a live video in an X-ray imaging apparatus according to an exemplary embodiment.

FIG. 4 is a diagram illustrating an X-ray imaging apparatus for performing radiography in an X-ray imaging apparatus according to an exemplary embodiment. FIG. 5 is a diagram illustrating an X-ray imaging apparatus for performing mammography in the X-ray imaging apparatus according to an exemplary embodiment. FIG. 6 is a diagram illustrating an X-ray imaging apparatus for imaging a live video in an X-ray imaging apparatus according to an exemplary embodiment.

As illustrated in FIG. 4, the X-ray imaging apparatus 100 according to an exemplary embodiment may be applied when radiography is performed.

The X-ray source 110 is connected to a ceiling of a radiation room and a height of the X-ray source 110 may be adjusted. When the X-ray source 110 is implemented as a sealing type, the X-ray source 110 may move forward, backward, left, and/or right along a guide rail provided in the ceiling of the radiation room.

An object 30 is positioned between the X-ray source 110 and the X-ray detector 120. When the X-ray imaging apparatus 100 performs radiography, the object 30 may be a chest, an arm, a leg, or the like.

In FIG. 4, the X-ray detector 120 is implemented as a stand type, but exemplary embodiments of the X-ray imaging apparatus 100 are not limited thereto, and the X-ray detector 120 may be implemented as, for example, a portable type.

The X-ray imaging apparatus 100 may further include a host device 140 configured to provide a user interface. The host device 140 is also called a workstation. The host device 140 may include a display 141 configured to display information on the X-ray imaging apparatus 100 or display a generated X-ray image and an input unit 142 configured to receive a user command.

The image processor 130 may be included as a component of the host device 140, but exemplary embodiments of the X-ray imaging apparatus 100 are not limited thereto. According to an exemplary embodiment, the image processor 130 may be included in another device as a component.

In addition, as illustrated in FIG. 5, the X-ray imaging apparatus 100 according to an exemplary embodiment may be applied when mammography is performed to image a breast. In this case, the breast, which is the object 30, is positioned between the X-ray source 110 and the X-ray detector 120. To perform vertical compression according to a characteristic of the breast 30, a compression paddle 107 may be further provided between the X-ray source 110 and the X-ray detector 120.

When the X-ray imaging apparatus 100 performs mammography, the host device 140 may be included in the X-ray imaging apparatus 100. A user may adjust a position of the compression paddle 107 through the input unit 142 of the host device 140.

In addition, the X-ray imaging apparatus 100 according to an exemplary embodiment may perform fluoroscopy to image a live X-ray video. For example, the X-ray imaging apparatus 100 may have a C-arm structure, as illustrated in FIG. 6. The X-ray source 110 and the X-ray detector 120 may be provided in each end of a C-arm 101 having a C shape. The C-arm 101 is connected to a main body 103 through a connecting shaft 105 and is rotatable in an orbital direction.

A patient table 109 is positioned between the X-ray source 110 and the X-ray detector 120. When the object is positioned on the patient table 109, the X-ray source 110 transmits X-rays onto the object, the X-ray detector 120 detects X-rays having penetrated through the object, and the X-ray image of the object is obtained by using the detected X-rays.

The X-ray imaging apparatus 100 may obtain a live X-ray video of the object. The user may input various control commands for X-ray imaging through the input unit 142, view the display 141 that includes a plurality of screens, and select to display several images for a procedure or diagnosis, and perform diagnosis or a procedure such as angiography.

Figure 7:
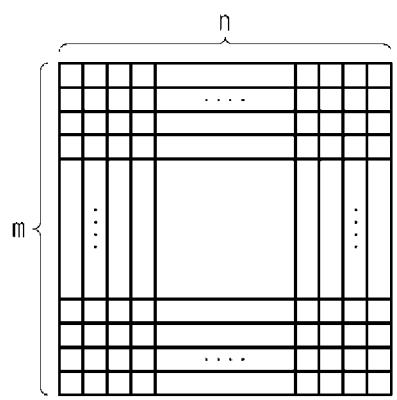
FIG. 7 is a diagram schematically illustrating a method of generating a high-resolution X-ray image.
Figure 7:
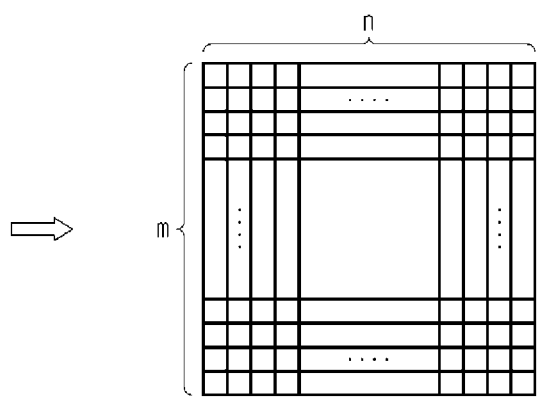
Figure 8:
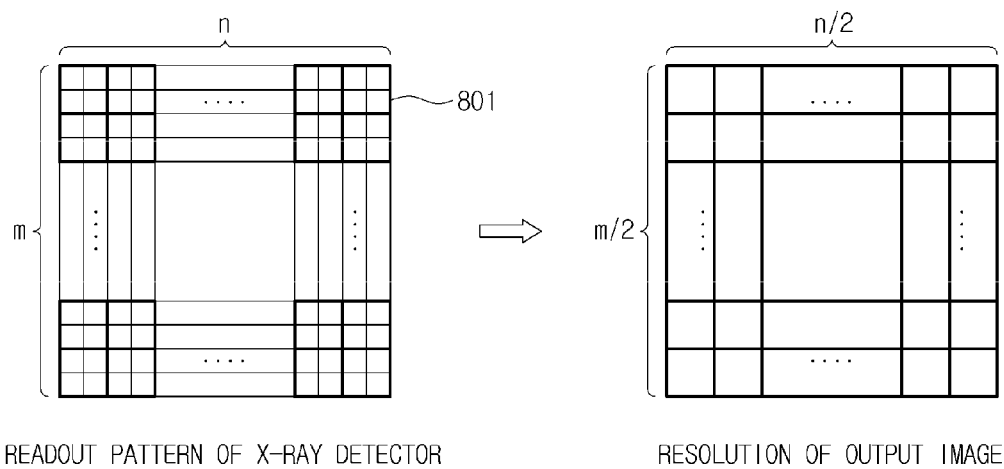
FIG. 8 is a diagram schematically illustrating a method of generating a low-resolution X-ray image.
Figure 9:
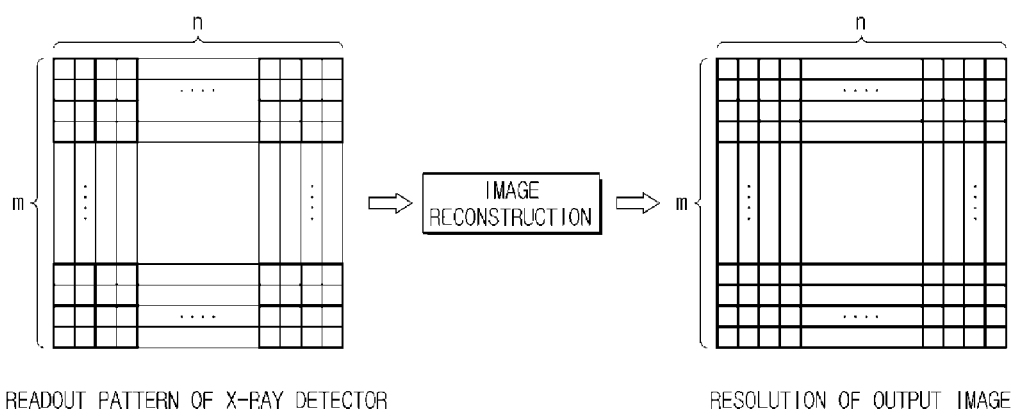
FIG. 9 is a diagram schematically illustrating a method of generating a high-resolution X-ray image in an X-ray imaging apparatus according to an exemplary embodiment.

FIG. 7 is a diagram schematically illustrating a method of generating a high-resolution X-ray image. FIG. 8 is a diagram schematically illustrating a method of generating a low-resolution X-ray image. FIG. 9 is a diagram schematically illustrating a method of generating a high-resolution X-ray image in an X-ray imaging apparatus according to an exemplary embodiment.

As illustrated in FIG. 7, when the X-ray detector is implemented in an m×n two-dimensional (2D) pixel array, a signal is readout from each of m×n pixels. That is, a signal readout from a single pixel is used as a pixel value of an output image, and a high-resolution X-ray image of an m×n resolution may be generated. In this case, the high-resolution X-ray image may be generated, however, a pixel size may be small. Therefore, a noise characteristic decreases and a large number of X-ray photons are needed to obtain an X-ray image. That is, an X-ray dose needs to increase to obtain an X-ray image.

Pixel binning is a method in which a plurality of adjacent pixels are combined to receive a signal to increase a frame rate and a noise characteristic, and implement low dose imaging. For example, when 2×2 binning is performed, as illustrated in FIG. 8, 2×2 adjacent pixels are combined to readout a signal therefrom. Thus, a unit of 2×2 adjacent pixels serve as a super pixel 801, and the resulting image has a resolution of m/2×n/2.

Pixel binning may be performed on the detection area to combine electric charges, may be performed on the readout circuit to combine electric charges or analog signals, and may be performed after signals pass through an analog-to-digital converter (ADC) and the converted digital signals are combined. When pixel binning is performed, a signal-to-noise ratio or a temporal resolution of the X-ray image increases but a spatial resolution may decrease.

Therefore, as illustrated in FIG. 9, in the X-ray imaging apparatus 100 according to an exemplary embodiment, when the X-ray detector 120 obtains the X-ray image, pixel binning is performed, and a low-resolution X-ray image that has an excellent frame rate and an excellent noise characteristic and can be imaged at a low X-ray dose is obtained. The image processor 130 may reconstruct a low-resolution X-ray image and generate an m×n high-resolution image without affecting a spatial resolution.

In the following exemplary embodiment, an X-ray image obtained by the X-ray detector 120 refers to a signal output from the readout circuit 124, that is, raw data, and an X-ray image generated by the image processor 130 refers to an image in which image processing such as image reconstruction is applied to the raw data.

In addition, a low resolution and a high resolution are relative terms. The low resolution represents a resolution lower than a resolution of the X-ray detector 120. The high resolution represents a resolution of the X-ray detector 120 or a resolution higher than the low resolution.

FIGS. 10A, 10B, 10C, and 10D are diagrams illustrating an example of changing a binning pattern when an X-ray detector performs 2×2 pixel binning. FIGS. 11A, 11B, 11C, and 11D are diagrams illustrating an example of changing a binning pattern when an X-ray detector performs 3×3 pixel binning. A position of each pixel in the X-ray detector 120 may be represented as 2D coordinates (row and column coordinates).

A combination of pixels forming one super pixel is referred to as a binning set (or binning unit). An overall pattern in which binning sets are combined in the X-ray detector 120 is referred to as a binning pattern.

The X-ray detector 120 performs pixel binning and obtains a low-resolution X-ray image, and may obtain a plurality of low-resolution X-ray images by changing the binning pattern. While the binning pattern is horizontally or vertically shifted, the plurality of low-resolution X-ray images may be obtained. For example, as illustrated in FIGS. 10A to 10D, four low-resolution X-ray images in total may be obtained while the binning pattern is shifted by one pixel horizontally or vertically. In this case, all of the four low-resolution X-ray images may be imaged at a low X-ray dose.

Figure 10A:
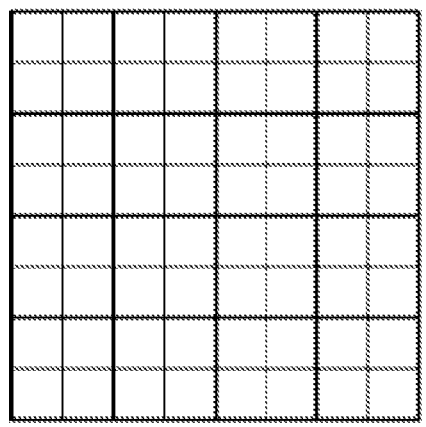
FIGS. 10A, 10B, 10C, and 10D are diagrams illustrating an example of changing a binning pattern when an X-ray detector performs 2×2 pixel binning.
Figure 10B:
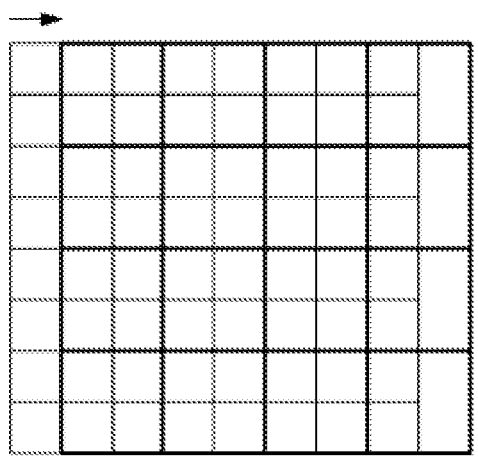
Figure 10C:
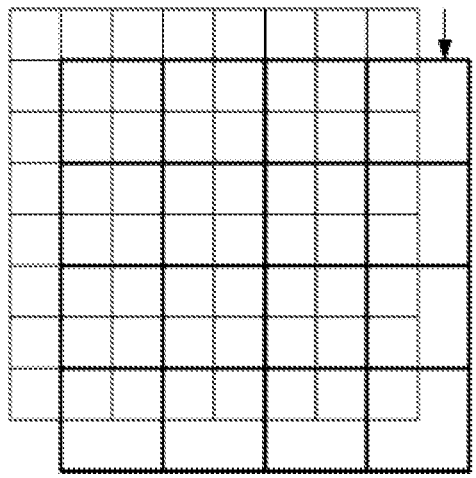
Figure 10D:
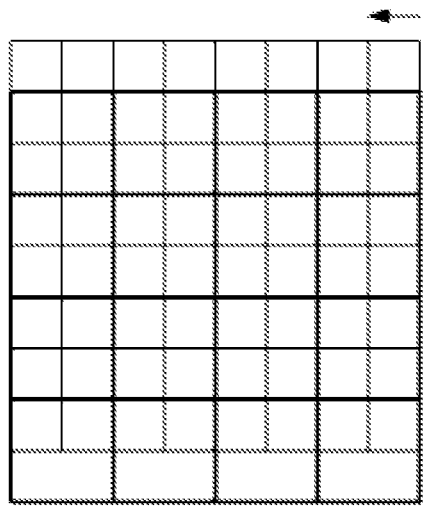

As illustrated in FIG. 10A, when the X-ray detector 120 performs 2×2 pixel binning, first imaging may be performed such that pixels of positions of (1,1), (1,2), (2,1), and (2,2) are combined as one super pixel and four adjacent pixels of the rest of the pixels are grouped and combined as one super pixel in a similar manner, and as illustrated in FIG. 10B, second imaging may be performed such that pixels of positions of (1,2), (1,3), (2,2), and (2,3) are combined as one super pixel and four adjacent pixels of the rest of the pixels are grouped and combined as one super pixel in a similar manner, and as illustrated in FIG. 10C, third imaging may be performed such that pixels of positions of (2,2), (2,3), (3,2), and (3,3) are combined as one super pixel and four adjacent pixels of the rest of the pixels are grouped and combined as one super pixel in a similar manner, and as illustrated in FIG. 10D, fourth imaging may be performed such that pixels of positions of (2,1), (2,2), (3,1), and (3,2) are combined as one super pixel and four adjacent pixels of the rest of the pixels are grouped and combined as one super pixel in a similar manner.

The 2×2 pixel binning is only an example of the X-ray imaging apparatus 100, and a size of the binning set may be variously adjusted in consideration of a characteristic of the object, an imaging purpose, and the like.

Figure 11A:
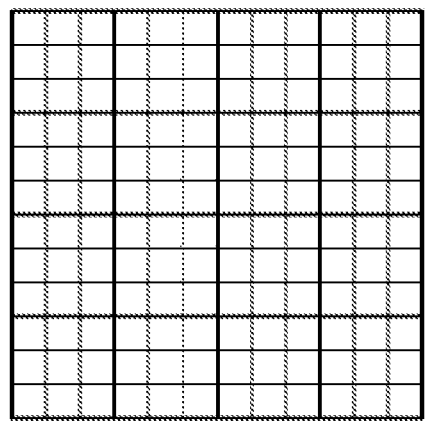
FIGS. 11A, 11B, 11C, and 11D are diagrams illustrating an example of changing a binning pattern applied when an X-ray detector performs 3×3 pixel binning.
Figure 11B:
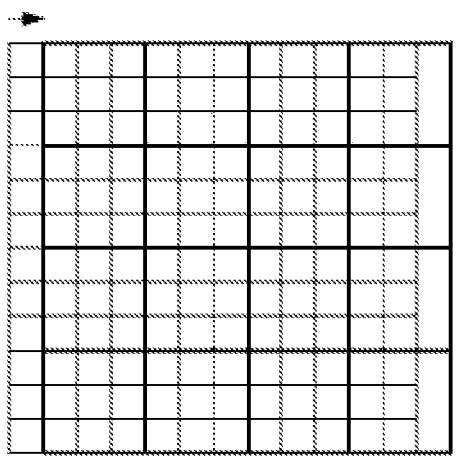
Figure 11C:
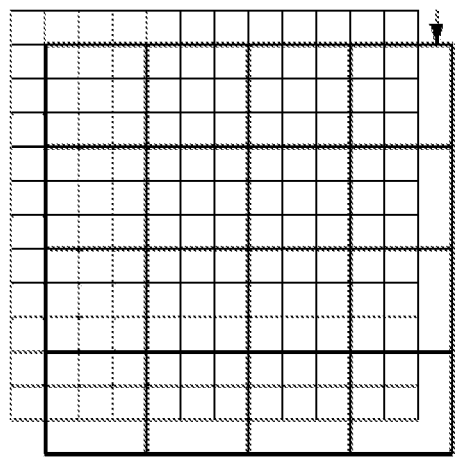
Figure 11D:
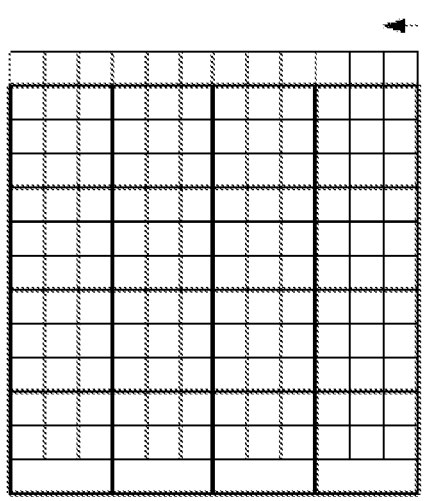

As illustrated in FIG. 11A, when the X-ray detector 120 performs 3×3 pixel binning, first imaging may be performed such that pixels of positions of (1,1), (1,2), (1,3), (2,1), (2,2), (2,3), (3,1), (3,2), and (3,3) are combined as one super pixel and nine adjacent pixels of the rest of the pixels are grouped and combined as one super pixel in a similar manner, and as illustrated in FIG. 11B, second imaging may be performed such that pixels of positions of (1,2), (1,3), (1,4), (2,2), (2,3), (2,4), (3,2), (3,3), and (3,4) are combined as one super pixel and nine adjacent pixels of the rest of the pixels are grouped and combined as one super pixel in a similar manner, and as illustrated in FIG. 11C, third imaging may be performed such that pixels of positions of (2,2), (2,3), (2,4), (3,2), (3,3), (3,4), (4,2), (4,3), and (4,4) are combined as one super pixel and nine adjacent pixels of the rest of the pixels are grouped and combined as one super pixel in a similar manner, and as illustrated in FIG. 11D, fourth imaging may be performed such that pixels of positions of (2,1), (2,2), (2,3), (3,1), (3,2), (3,3), (4,1), (4,2), and (4,3) are combined as one super pixel and nine adjacent pixels of the rest of the pixels are grouped and combined as one super pixel in a similar manner.

The image processor 130 may reconstruct the plurality of low-resolution X-ray images obtained by the X-ray detector 120 and generate the high-resolution X-ray image. A detailed image reconstructing process will be described below.

In an exemplary embodiment, when imaging of an object is changed, it can be understood as a change in the binning pattern or a shift of the binning pattern. Through the change in the binning pattern, a plurality of X-ray images having different pieces of information on the same scene may be obtained. Accordingly, it is possible to obtain an effect of obtaining the X-ray image as if the X-ray detector 120 physically moves. In particular, as shown in FIGS. 10 and 11, when the binning pattern is changed, it is possible to obtain an effect of physically moving the X-ray detector 120 by a size of one pixel.

Since the X-ray detector 120 is not actually moved, no additional component for moving the X-ray detector 120 is needed, and there is no concern for possible errors or mismatches that may occur in a process of moving the X-ray detector 120 having a large volume by a pixel size.

In the examples of FIGS. 10 and 11, an imaging order is not limited to an order of first imaging, second imaging, third imaging, and fourth imaging. Only the binning pattern in each imaging needs to be changed as illustrated in FIGS. 10 and 11.

In addition, a shift size of the binning pattern is not limited to one pixel, but shift may be performed by any size of one pixel or more.

To obtain the plurality of low-resolution X-ray images, the X-ray imaging apparatus 100 may continuously perform X-ray imaging. For this purpose, the X-ray source 110 may continuously transmit X-rays onto the object 30 and transmit X-rays using a pulse method at predetermined time intervals. Since the X-ray detector 120 performs pixel binning, the X-ray source 110 may transmit X-rays of a low dose.

The X-ray detector 120 is not limited to obtaining four low-resolution X-ray images as shown in FIGS. 10 and 11, but may obtain fewer or more than four low-resolution X-ray images.

However, in the following exemplary embodiment, for illustrative purposes, a case in which the binning pattern is shifted by one pixel and four low-resolution X-ray images are obtained will be described.

Hereinafter, an operation and a structure of the X-ray detector 120 capable of switching the binning pattern will be described.

Figure 12:
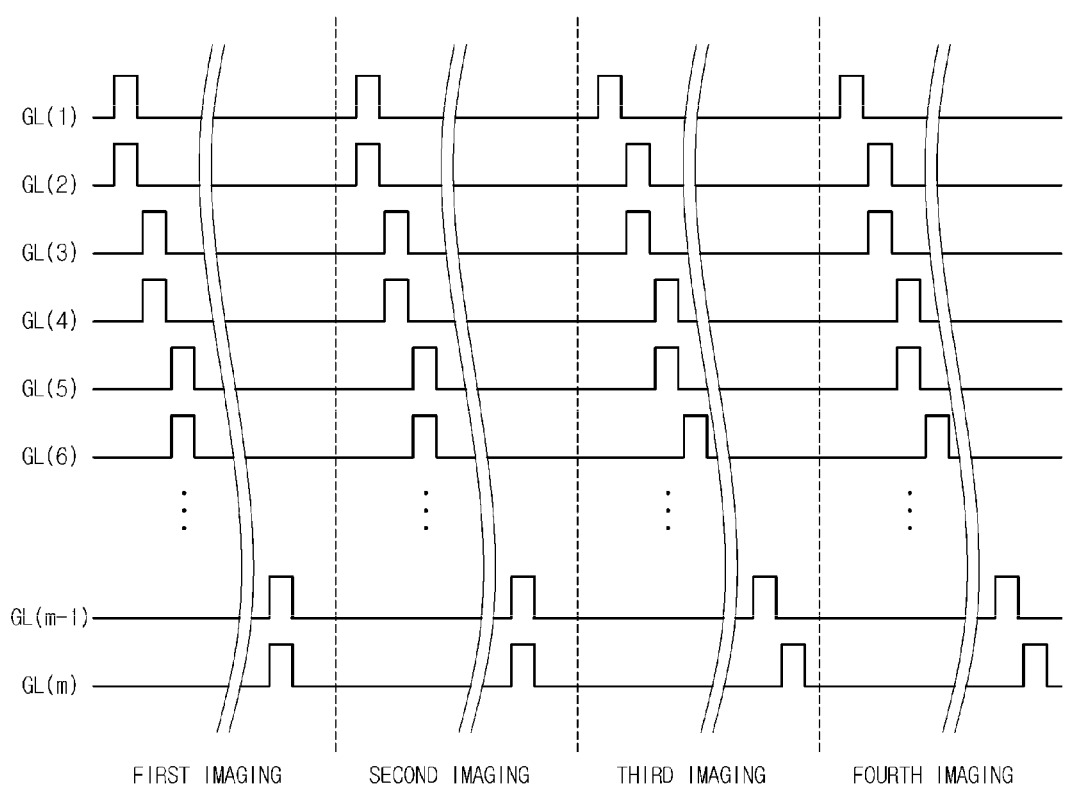
FIG. 12 is a timing diagram illustrating a signal applied to each gate line of an X-ray detector to change a binning pattern according to an exemplary embodiment.

FIG. 12 is a timing diagram illustrating a signal applied to each gate line of an X-ray detector to change a binning pattern according to an exemplary embodiment.

When no pixel binning is performed, a gate signal is sequentially applied from a first gate line GL(1) to an n-th gate line GL(n). When the X-ray detector 120 performs pixel binning, a gate signal is simultaneously applied to a plurality of gate lines GL.

A case in which 2×2 pixel binning is applied, and first imaging, second imaging, third imaging, and fourth imaging are sequentially performed as illustrated in FIGS. 10A to 10D will be described.

As illustrated in FIG. 12, to perform first imaging, a gate signal is simultaneously applied to the first gate line GL(1) and the second gate line GL(2), and a gate signal is simultaneously applied to the third gate line GL(3) and the fourth gate line GL(4). Also, a gate signal is simultaneously applied to a group of two adjacent gate lines in the same manner, from the fifth gate line GL(5) to the m-th gate line GL(m).

A frame time (FT) that is a time taken for obtaining one X-ray image is determined by a line time (LT) that is a gate signal application time per line and the number of lines (m). Here, the line refers to a row of a gate line. Therefore, it can be understood that a frame time when pixel binning is performed is less than a frame time when no pixel binning is performed. Accordingly, it is possible to increase the frame rate when an X-ray video is obtained.

After one X-ray image is obtained through first imaging, the binning pattern is changed and second imaging is performed.

In the binning pattern of second imaging, positions of pixels forming a super pixel of a position of (1,1) in a super pixel array correspond to (1,2), (1,3), (2,2), and (2,3), as illustrated in FIG. 10B. Therefore, as in the first imaging, a gate signal is simultaneously applied to a group of two gate lines from the first gate line GL(1) to the m-th gate line GL(m). A method of applying a gate signal to a gate line is the same as in the first imaging and the second imaging, but a method of obtaining a signal from a data line is different, as will be described below.

Also, in the binning pattern of third imaging, positions of pixels forming a super pixel of a position of (1,1) in a super pixel array correspond to (2,2), (2,3), (3,2), and (3,3), as illustrated in FIG. 10C. Therefore, after a gate signal is applied to the first gate line GL(1), a gate signal is simultaneously applied to the second gate line GL(2) and the third gate line GL(3), and a gate signal is simultaneously applied to the fourth gate line GL(4) and the fifth gate line GL(5). A gate signal is also applied to the rest of the gate lines by grouping the gate lines by two.

Also, in the binning pattern of fourth imaging, positions of pixels forming a super pixel of a position of (1,1) in a super pixel array correspond to (2,1), (2,2), (3,1), and (3,2), as illustrated in FIG. 10D. Therefore, as in the third imaging, after a gate signal is applied to the first gate line GL(1), a gate signal is simultaneously applied to the second gate line GL(2) and the third gate line GL(3), and a gate signal is simultaneously applied to the fourth gate line GL(4) and the fifth gate line GL(5). A gate signal is also applied to the rest of the gate lines by grouping the gate lines by two.

When 3×3 pixel binning is performed, a gate signal is simultaneously applied to three gate lines but a combination of gate lines to which a gate signal is simultaneously applied may be varied according to a binning pattern.

As illustrated in FIG. 3, the X-ray detector 120 includes the switch 123 configured to connect the detection area 121 and the readout circuit 124. The switch 123 combines signals output from the plurality of data lines DL into one signal according to the binning pattern. Hereinafter, a structure and an operation of the switch 123 will be described in detail.

Figure 13:
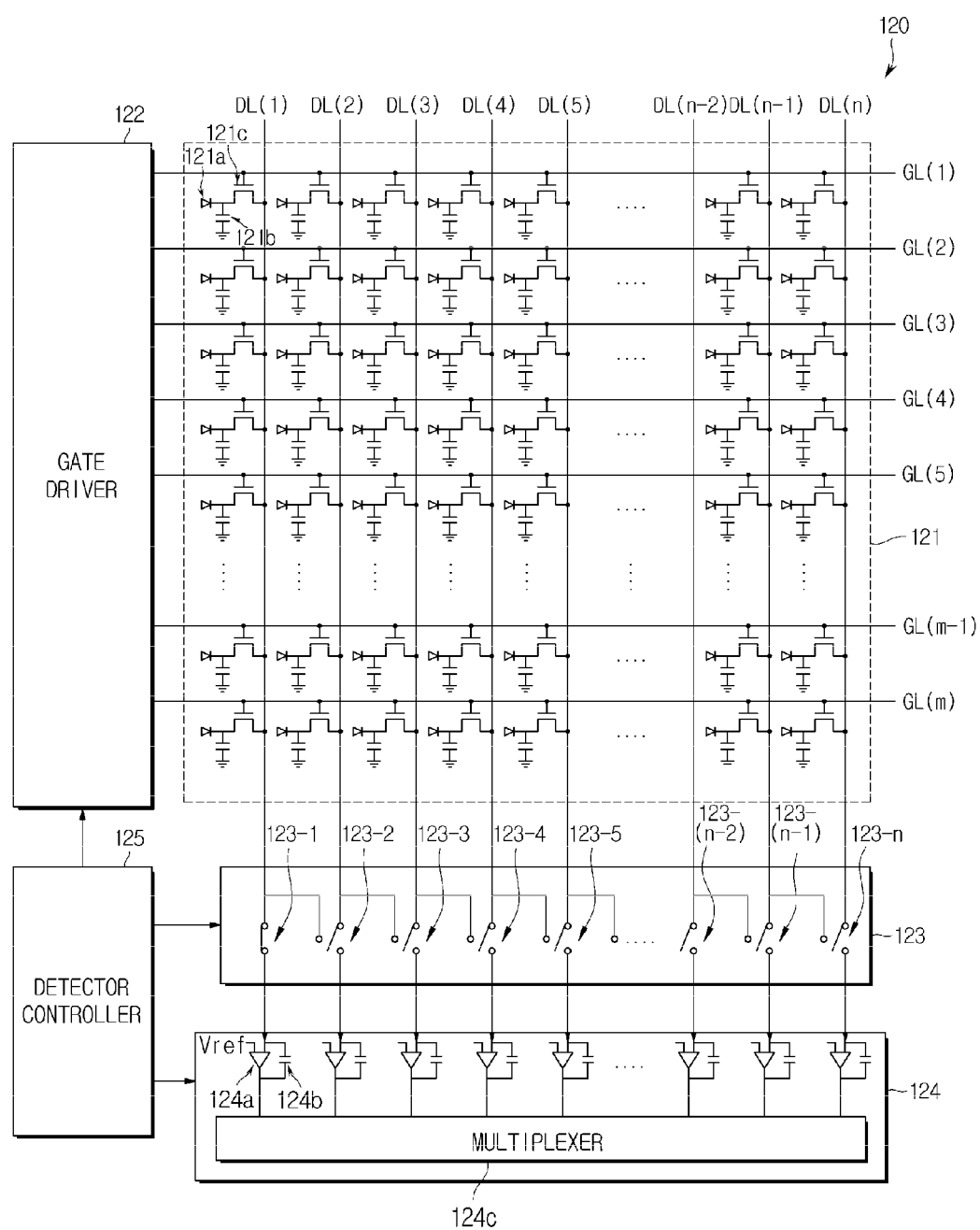
FIG. 13 is a diagram illustrating a structure of an X-ray detector according to an exemplary embodiment.

FIG. 13 is a diagram illustrating a structure of an X-ray detector according to an example.

Electrical signals delivered through n data lines DL(1), DL(2), . . . , and DL(n) (collectively referred to as "DL") are input to the readout circuit 124. The switch 123 is connected to an end portion of the data line DL and may selectively connect the data line DL and the readout circuit 124.

For this purpose, as illustrated in FIG. 13, the switch 123 may include n switching elements 123-1, 123-2, . . . , and 123-n corresponding to the n data lines DL, respectively. A type of the switching element is not limited. For example, a non-contact switch using a semiconductor device such as a transistor or a thyristor may be used, and a mechanical switch having a contact such as a relay switch may also be used.

In this example, as illustrated in FIG. 13, a two-way switch capable of selectively connecting the data lines DL is used.

For example, the second switching element 123-2 may connect the second data line DL(2) to the readout circuit 124 or to the first data line DL(1). In addition, subsequent switching elements 123-3, 123-4, . . . , 123-n may connect the readout circuit 124 to a data line connected to the corresponding switching element or to an adjacent data line.

Although it is described that the two-way switch is implemented in the second switching element 123-2 and subsequent switching elements 123-3, 123-4, . . . , 123-n to selectively connect current data lines to previous data lines in FIG. 13, the two-way switch may be implemented in the first switching element 123-1 and subsequent switching elements 123-2, 123-3, . . . , 123-n to selective connect the current data lines to next data lines.

A detailed operation of the switching element according to the binning pattern according to an exemplary embodiment will be described below.

The readout circuit 124 may include m amplifiers 124a corresponding to n data lines, respectively, and a capacitor 121b connected to an input terminal and an output terminal of each of the amplifiers 124a. In addition, although not illustrated, both ends of the capacitor 121b may be connected using a switch, and a voltage charged in the capacitor 121b may be discharged through the switch.

The amplifier 124a includes a first input terminal connected to the switch 123, a second input terminal to which a reference voltage Vref is applied, and an output terminal. For example, the first input terminal may be a negative terminal of the amplifier 124a and the second input terminal may be a positive terminal of the amplifier 124a.

An output terminal of the amplifier 124a may be connected to a multiplexer 124c. However, according to an exemplary embodiment, no multiplexer may be provided in the X-ray detector 120 and signals from each column may be output in parallel.

An electrical signal output from the amplifier 124a is input to the multiplexer 124c and the multiplexer 124c sequentially transmits the input electrical signal to the image processor 130. For this purpose, the multiplexer 124c may be implemented as an n-to-1 multiplexer (MUX) by including switches corresponding to each of the amplifiers 124a.

The detector controller 125 may control the gate driver 122, the switch 123, and the readout circuit 124.

A case in which a gate signal is input according to the timing diagram in FIG. 12 to change the binning pattern in the order of binning patterns as shown in FIGS. 10A, 10B, 10C, and 10D will be described as an example of an operation of the switching element according to the binning pattern.

Figure 14:
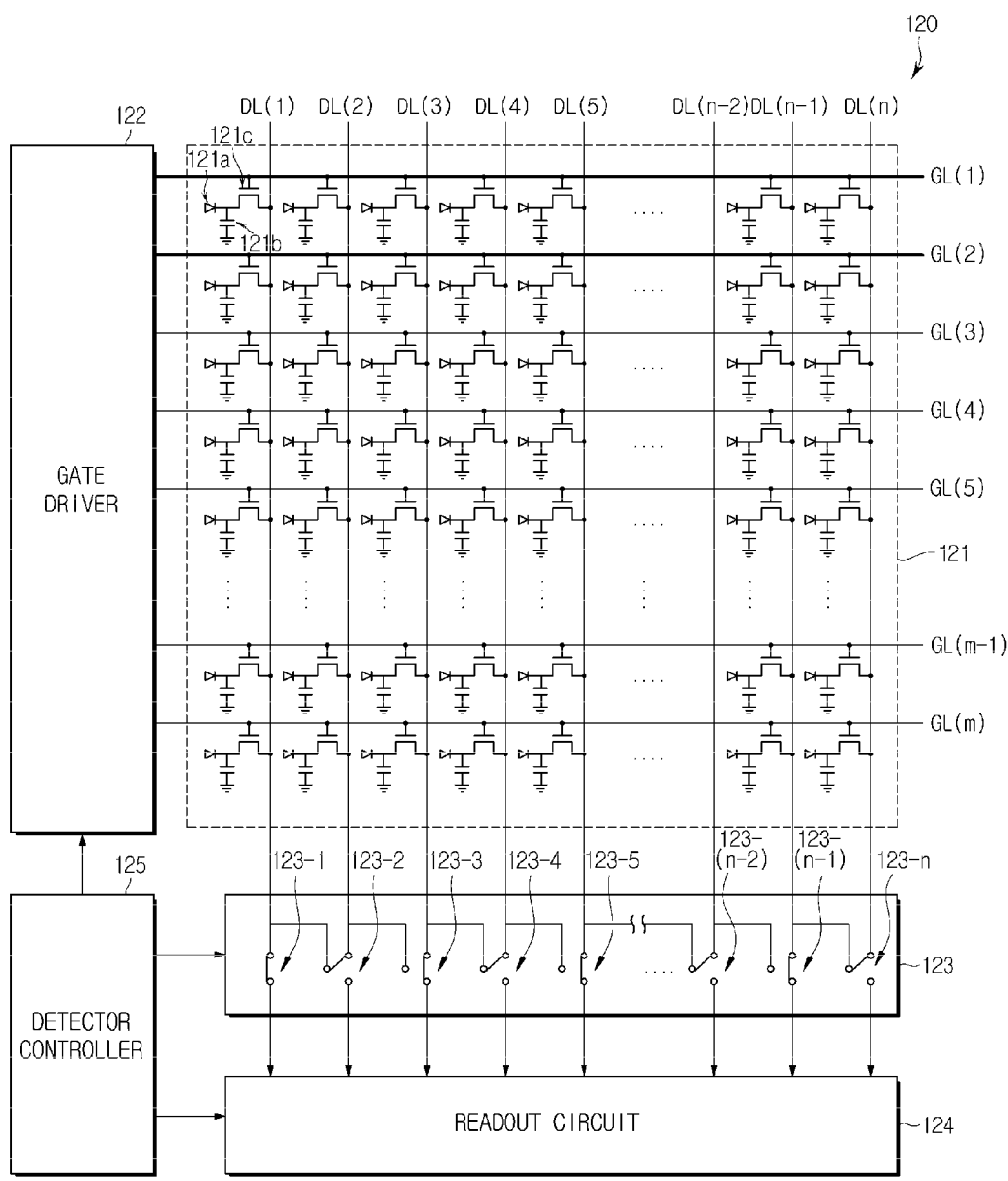
FIGS. 14 and 15 are diagrams illustrating an operation of a switching element when first imaging is performed according to an exemplary embodiment.
Figure 15:
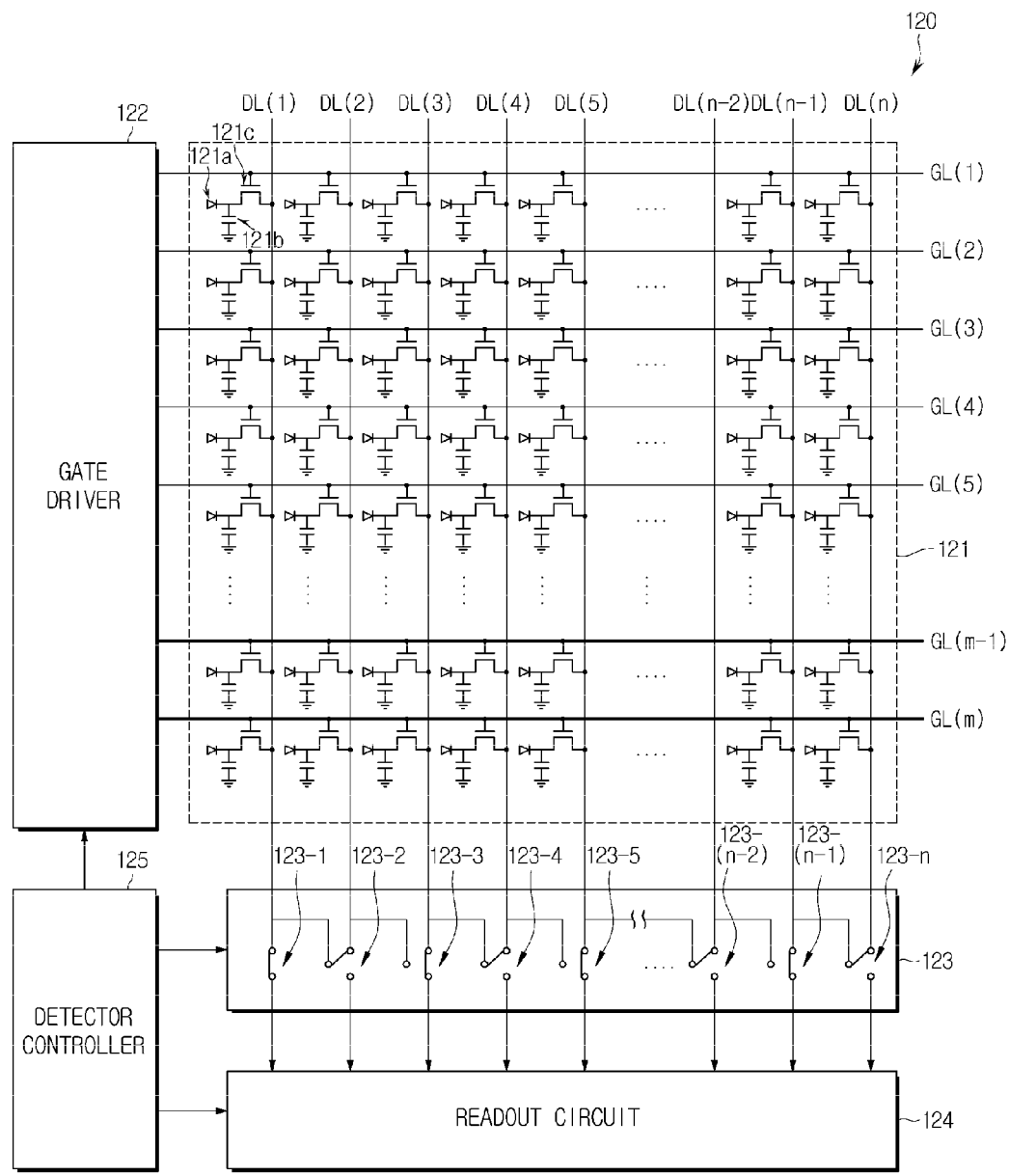

FIGS. 14 and 15 are diagrams illustrating an operation of a switching element when first imaging as shown in FIG. 10A is performed.

As illustrated in FIG. 14, to obtain signals from pixels positioned in a first row and a second row, a gate signal is simultaneously applied to the first gate line GL(1) and the second gate line GL(2) (represented in bold lines). While the gate signal is applied, a signal is obtained from corresponding data lines from the first data line DL(1) to the n-th data line DL(n).

In the first imaging, to obtain a signal from a super pixel of a position of (1,1) in a super pixel array, while a gate signal is simultaneously applied to the first gate line GL(1) and the second gate line GL(2), the first switching element 123-1 connected to the first data line DL(1) is turned on and the second switching element 123-2 connected to the second data line DL(2) is connected to the first data line DL(1). Therefore, a signal may be simultaneously obtained from four pixels of positions of (1,1), (1,2), (2,1), and (2,2). That is, the signals obtained from the four pixels may be combined into one signal and input to the readout circuit 124.

As illustrated in FIG. 13, when the readout circuit 124 includes the amplifier 124a corresponding to each data line, since signals obtained from four pixels are combined into one signal and input to amplifier 124a, a noise characteristic may be improved.

To obtain a signal from a super pixel of a position of (1,2) in a super pixel array, the third switching element 123-3 connected to the third data line DL(3) is connected to the readout circuit 124 and the fourth switching element 123-4 connected to the fourth data line DL(4) is connected to the third data line DL(3). Therefore, signals obtained from four pixels of positions of (1,3), (1,4), (2,3), and (2,4) are combined into one signal and input to the readout circuit 124.

From a super pixel of a position of (1,3) to a super pixel of a position of (1,n/2−1) in a super pixel array, the switching element is switched in a similar manner, and two data lines may be grouped together to output signals.

Also, to obtain a signal from a super pixel of a position of (1, n/2) in a super pixel array, while a gate signal is applied to the first gate line GL(1) and the second gate line GL(2), the (n−1)-th switching element 123-(n−1) connected to the (n−1)-th data line DL(n−1) is connected to the readout circuit 124 and the n-th switching element 123-n connected to the n-th data line DL(n) is connected to the (n−1)-th data line DL(n−1). Therefore, signals obtained from four pixels of positions of (1,n−1), (1,n), (2,n−1), and (2,n) may be combined into one signal and input to the readout circuit 124.

The first switching element 123-1 to the n-th switching element 123-n may be simultaneously turned on or may be turned on with a time difference.

When signals of the first row and the second row are obtained, signals are sequentially obtained from the rest of the rows that are grouped by two.

As illustrated in FIG. 15, to obtain signals from pixels positioned in an (m−1)-th row and an m-th row, a gate signal is simultaneously applied to the (m−1)-th gate line GL(m−1) and the m-th gate line GL(m). While the gate signal is applied, signals are obtained from corresponding data lines from the first data line DL(1) to the n-th data line DL(n) that are grouped by two.

To obtain a signal from a super pixel of a position of (m/2,1) in a super pixel array, while a gate signal is applied to the (m−1)-th gate line GL(m−1) and the m-th gate line GL(m), the first switching element 123-1 is turned on and the second switching element 123-2 is connected to the first data line DL(1). Therefore, signals may be simultaneously obtained from four pixels of positions of (m−1,1), (m−1,2), (m,1), and (m,2). That is, signals obtained from the four pixels may be combined into one signal and input to the readout circuit 124.

To obtain a signal from a super pixel of a position of (m/2,2) in a super pixel array, the third switching element 123-3 is connected to the readout circuit 124 and the fourth switching element 123-4 is connected to the third data line DL(3). Therefore, signals obtained from four pixels of positions of (m−1,3), (m−1,4), (m,3), and (m,4) may be combined into one signal and input to the readout circuit 124.

From a super pixel of a position of (m/2,3) to a super pixel of a position of (m/2,n/2−1) in a super pixel array, the switching element is switched in a similar manner, and two data lines may be grouped together to output signals.

Also, to obtain a signal from a super pixel of a position of (m/2,n/2) in a super pixel array, while a gate signal is applied to the (m−1)-th gate line GL(m−1) and the m-th gate line GL(m), the (n−1)-th switching element 123-(n−1) connected to the (n−1)-th data line DL(n−1) is connected to the readout circuit 124 and the n-th switching element 123-n connected to the n-th data line DL(n) is connected to the (n−1)-th data line DL(n−1). Therefore, signals obtained from four pixels of positions of (m−1,n−1), (m−1,n), (m,n−1), and (m,n) may be combined into one signal and input to the readout circuit 124.

Figure 16:
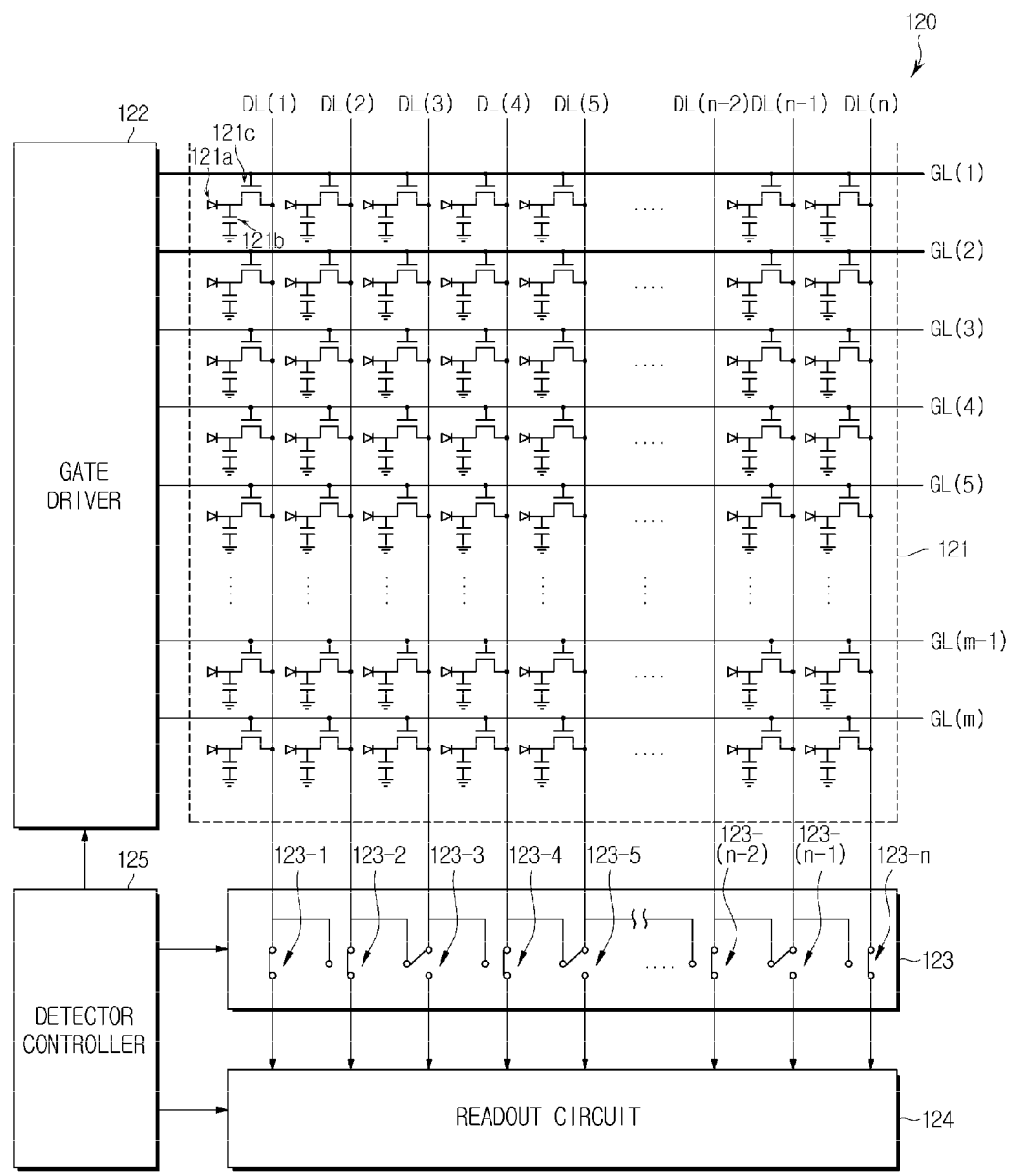
FIGS. 16 and 17 are diagrams illustrating an operation of a switching element when second imaging is performed according to an exemplary embodiment.
Figure 17:
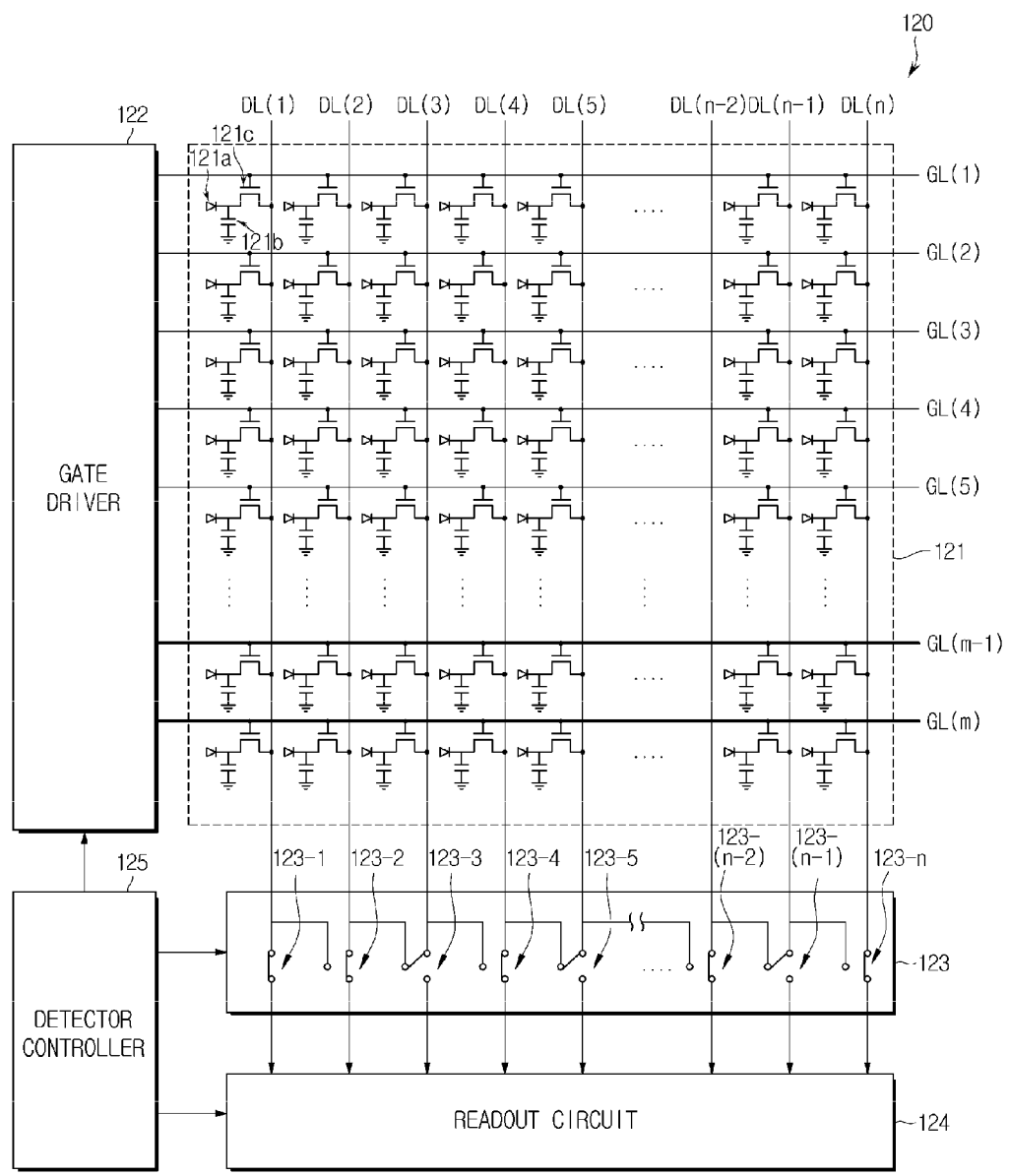

FIGS. 16 and 17 are diagrams illustrating an operation of a switching element when second imaging as shown in FIG. 10B is performed.

As illustrated in FIG. 16, in second imaging, to obtain a signal from a super pixel of a position of (1,1) in a super pixel array, a gate signal is simultaneously applied to the first gate line GL(1) and the second gate line GL(2). While the gate signal is applied, the second switching element 123-2 is connected to the readout circuit 124 and the third switching element 123-3 is connected to the second data line DL(2). Therefore, signals obtained from four pixels of positions of (1,2), (1,3), (2,2), and (2,3) may be combined into one signal and input to the readout circuit 124.

To obtain a signal from a super pixel of a position of (1,2) in a super pixel array, the fourth switching element 123-4 is connected to the readout circuit 124 and the fifth switching element 123-5 is connected to the fourth data line DL(4). Therefore, signals obtained from four pixels of positions of (1,4), (1,5), (2,4), and (2,5) may be combined into one signal and input to the readout circuit 124.

From a super pixel of a position of (1,3) to a super pixel of a position of (1,n/2−2) in a super pixel array, the switching element is switched in a similar manner, and two data lines may be grouped together to output signals.

Also, to obtain a signal from a super pixel of a position of (1,n/2−1) in a super pixel array, while a gate signal is applied to the first gate line GL(1) and the second gate line GL(2), the (n−2)-th switching element 123-(n−2) is connected to the readout circuit 124 and the (n−1)-th switching element 123-(n−1) is connected to the (n−2)-th data line DL(n−2). Therefore, signals obtained from four sub pixels of positions of (1,n−2), (1,n−1), (2,n−2), and (2,n−1) may be combined into one signal and input to the readout circuit 124.

When signals of the first row and the second row are obtained, signals are sequentially obtained from the rest of the rows that are grouped by two.

As illustrated in FIG. 17, to obtain signals from pixels positioned in an (m−1)-th row and an m-th row, a gate signal is simultaneously applied to the (m−1)-th gate line GL(m−1) and the m-th gate line GL(m). While the gate signal is applied, signals are obtained from corresponding data lines from the first data line DL(1) to the n-th data line DL(n) that are grouped by two.

To obtain a signal from a super pixel of a position of (m/2,1) in a super pixel array, while a gate signal is applied to the (m−1)-th gate line GL(m−1) and the m-th gate line GL(m), the second switching element 123-2 is connected to the readout circuit 124 and the third switching element 123-3 is connected to the second data line DL(2). Therefore, signals obtained from four pixels of positions of (m−1,2), (m−1,3), (m,2), and (m,3) may be combined into one signal and input to the readout circuit 124.

To obtain a signal from a super pixel of a position of (m/2,2) in a super pixel array, the fourth switching element 123-4 is connected to the readout circuit 124 and the fifth switching element 123-5 is connected to the fourth data line DL(4). Therefore, signals obtained from four pixels of positions of (m−1,4), (m−1,5), (m,4), and (m,5) may be combined into one signal and input to the readout circuit 124.

From a super pixel of a position of (m/2,3) to a super pixel of a position of (m/2,n/2−2) in a super pixel array, the switching element is switched in a similar manner, and two data lines may be grouped together to output signals.

Also, to obtain a signal from a super pixel of a position of (m/2,n/2−1) in a super pixel array, while a gate signal is applied to the (m−1)-th gate line GL(m−1) and the m-th gate line GL(m), the n−2-th switching element 123-($n$−2) is connected to the readout circuit 124 and the (n−1)-th switching element 123-($n$−1) is connected to the (n−2)-th data line DL(n−2). Therefore, signals obtained from four pixels of positions of (m−1,n−2), (m−1,n−1), (m,n−2), and (m,n−1) may be combined into one signal and input to the readout circuit 124.

In addition, the first switching element 123-1 and the n-th switching element 123-$n$ are connected to the readout circuit 124. Signals obtained from the first data line DL(1) and the n-th data line DL(n) may be input to the readout circuit 124.

In the second imaging, signals obtained from the first data line DL(1) and the n-th data line DL(n) are the result of 2×1 pixel binning. Therefore, to further increase a frame rate, the first switching element 123-1 and/or the n-th switching element 123-$n$ may be turned off.

Figure 18:
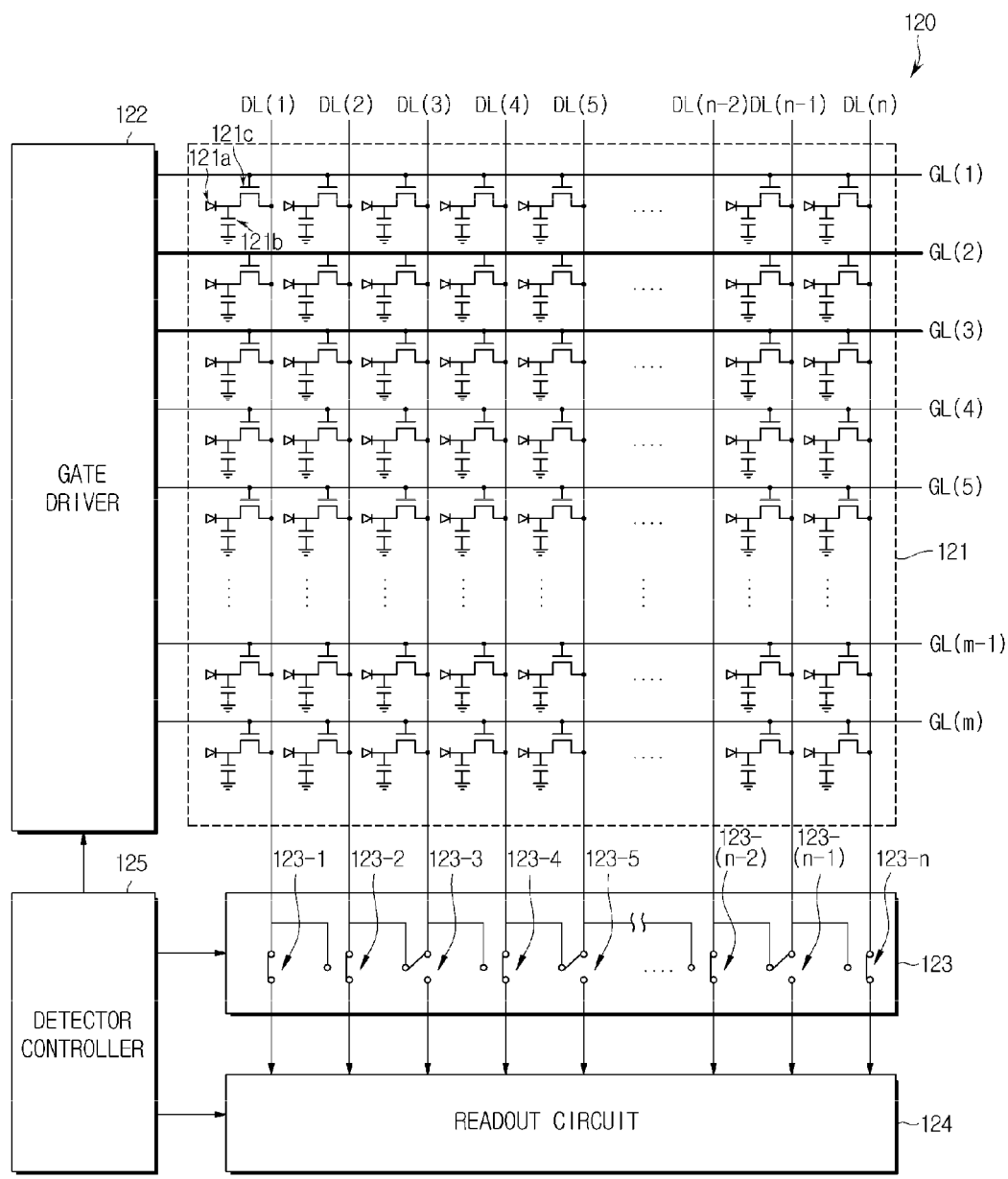
FIGS. 18 and 19 are diagrams illustrating an operation of a switching element when third imaging is performed according to an exemplary embodiment.
Figure 19:
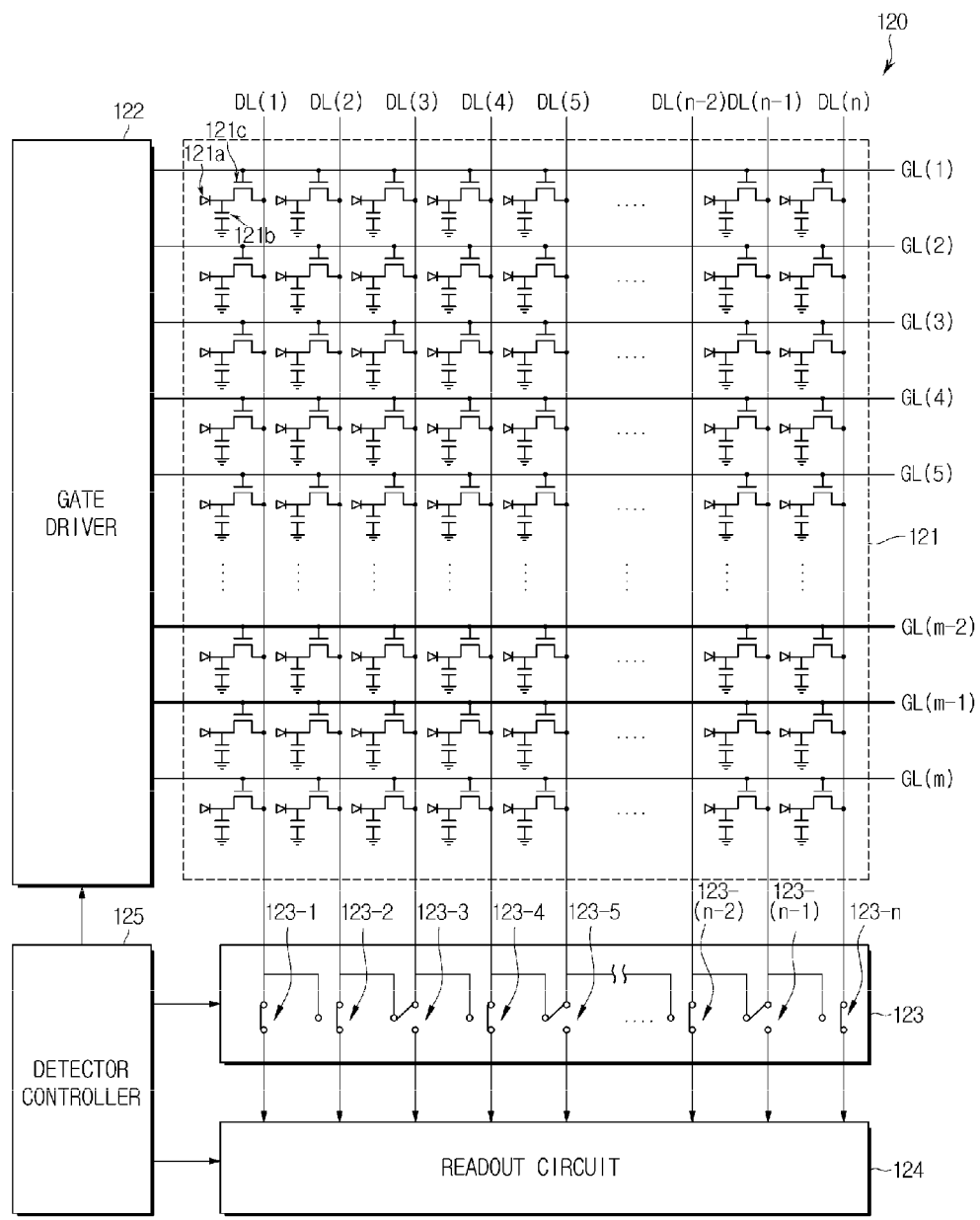

FIGS. 18 and 19 are diagrams illustrating an operation of a switching element when third imaging as shown in FIG. 10C is performed.

As illustrated in FIG. 18, in third imaging, to obtain a signal from a super pixel of a position of (1,1) in a super pixel array, a gate signal is simultaneously applied to the second gate line GL(2) and the third gate line GL(3). While the gate signal is applied, the second switching element 123-2 is connected to the readout circuit 124 and the third switching element 123-3 is connected to the second data line DL(2). Therefore, signals obtained from four pixels of positions of (2,2), (2,3), (3,2), and (3,3) are combined into one signal and are input to the readout circuit 124.

To obtain a signal from a super pixel of a position of (1,2) in a super pixel array, the fourth switching element 123-4 is connected to the readout circuit 124 and the fifth switching element 123-5 is connected to the fourth data line DL(4). Therefore, signals obtained from four pixels of positions of (2,4), (2,5), (3,4), and (3,5) may be combined into one signal and input to the readout circuit 124.

From a super pixel of a position of (1,3) to a super pixel of a position of (1,n/2−2) in a super pixel array, the switching element is switched in a similar manner, and two data lines may be grouped together to output signals.

Also, to obtain a signal from a super pixel of a position of (1,n/2−1) in a super pixel array, while a gate signal is applied to the second gate line GL(2) and the third gate line GL(3), the n−2-th switching element 123-($n$−2) is connected to the readout circuit 124 and the (n−1)-th switching element 123-($n$−1) is connected to the (n−2)-th data line DL(n−2). Therefore, signals obtained from four sub pixels of positions of (2,n−2), (2,n−1), (3,n−2), and (3,n−1) may be combined into one signal and input to the readout circuit 124.

When signals of the second row and the third row are obtained, signals are sequentially obtained from the rest of the rows that are grouped by two.

As illustrated in FIG. 19, to obtain a signal from a super pixel of a position of (m/2−1,1) in a super pixel array, a gate signal is applied to the (m−2)-th gate line GL(m−2) and the (m−1)-th gate line GL(m−1). While the gate signal is applied, the second switching element 123-2 is connected to the readout circuit 124 and the third switching element 123-3 is connected to the second data line DL(2). Therefore, signals obtained from four pixels of positions of (m−2,2), (m−2,3), (m−1,2), and (m−1,3) may be combined into one signal and input to the readout circuit 124.

To obtain a signal from a super pixel of a position of (m/2−1,2) in a super pixel array, the fourth switching element 123-4 is connected to the readout circuit 124 and the fifth switching element 123-5 is connected to the fourth data line DL(4). Therefore, signals obtained from four pixels of positions of (m−2,4), (m−2,5), (m−1,4), and (m−1,5) may be combined into one signal and input to an amplifier 124$a$-4 of the readout circuit 124.

From a super pixel of a position of (m/2−1,3) to a super pixel of a position of (m/2−1,n/2−2) in a super pixel array, the switching element is switched in a similar manner and two data lines may be grouped together to output signals.

Also, to obtain a signal from a super pixel of a position of (m/2−1,n/2−1) in a super pixel array, while a gate signal is applied to the (m−2)-th gate line GL(m−2) and the (m−1)-th gate line GL(m−1), the n−2-th switching element 123-($n$−2) is connected to the readout circuit 124 and the (n−1)-th switching element 123-($n$−1) is connected to the (n−2)-th data line DL(n−2). Therefore, signals obtained from four pixels of positions of (m−2,n−2), (m−2,n−1), (m−1,n−2), and (m−1,n−1) may be combined into one signal and input to the readout circuit 124.

In addition, the first switching element 123-1 and the n-th switching element 123-$n$ are connected to the readout circuit 124 and signals obtained from the first data line DL(1) and the n-th data line DL(n) may be input to the readout circuit 124.

In addition, a gate signal is applied to the first gate line GL(1) and the n-th gate line GL(n), and a process of obtaining a signal by grouping two data lines may be applied.

However, in third imaging, signals obtained from the first data line DL(1) and the n-th data line DL(n) are the result of 2×1 pixel binning. Therefore, to further increase a frame rate, the first switching element 123-1 and/or the n-th switching element 123-$n$ may be turned off.

In addition, signals obtained from the first gate line GL(1) and the m-th gate line GL(m) are the result of 1×2 pixel binning. Therefore, to further increase a frame rate, no gate signal may be applied to the first gate line GL(1) and/or the m-th gate line GL(m).

Figure 20:
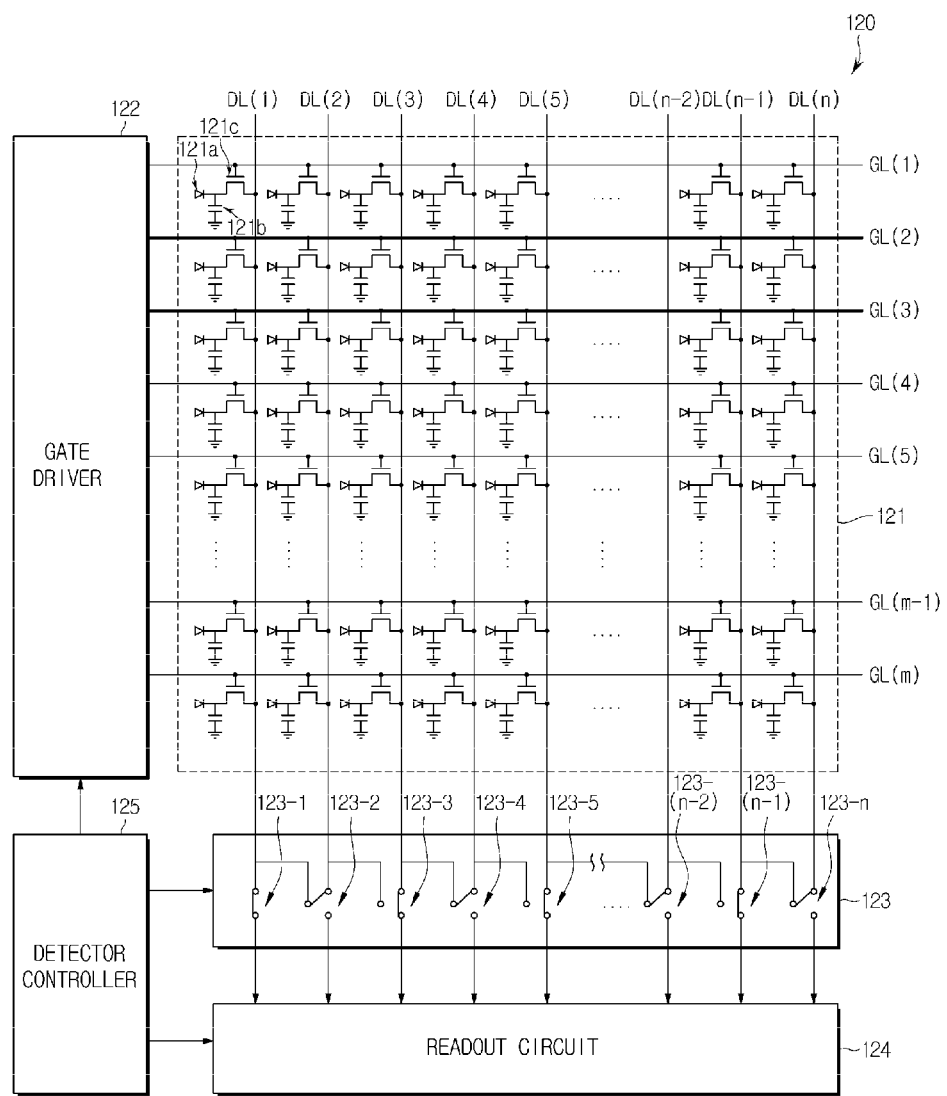
FIGS. 20 and 21 are diagrams illustrating an operation of a switching element when fourth imaging is performed according to an exemplary embodiment.
Figure 21:
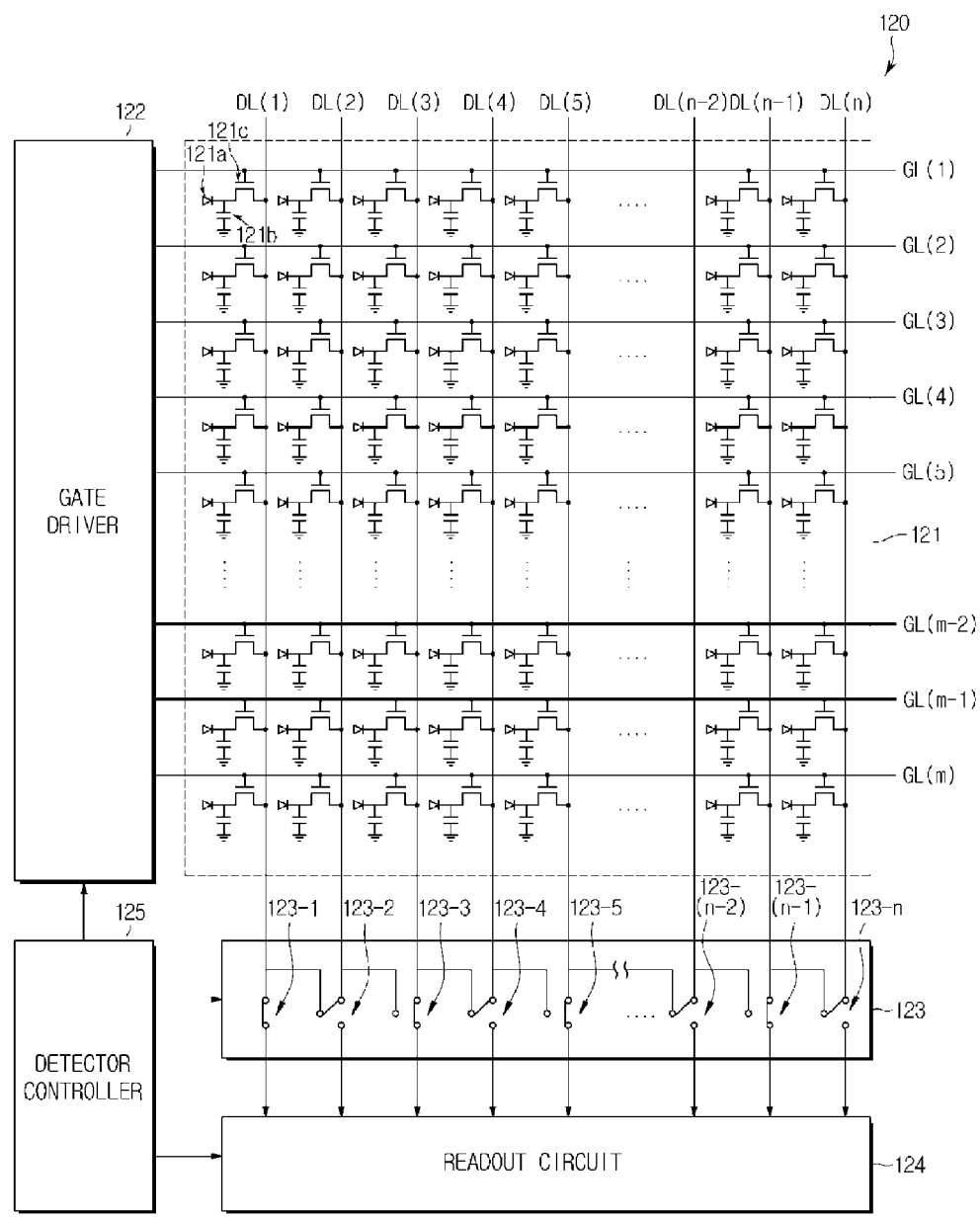

FIGS. 20 and 21 are diagrams illustrating an operation of a switching element applied when fourth imaging as shown in FIG. 10D is performed.

As illustrated in FIG. 20, in fourth imaging, to obtain a signal from a super pixel of a position of (1,1) in a super pixel array, a gate signal is simultaneously applied to the second gate line GL(2) and the third gate line GL(3). While the gate signal is applied, the first switching element 123-1 is turned on and the second switching element 123-2 is connected to the first data line DL(1). Therefore, signals obtained from four pixels of positions of (2,1), (2,2), (3,1), and (3,2) may be combined into one signal and input to the readout circuit 124.

To obtain a signal from a super pixel of a position of (1,2) in a super pixel array, the third switching element 123-3 is connected to the readout circuit 124 and the fourth switching element 123-4 is connected to the third data line DL(3). Therefore, signals obtained from four pixels of positions of (2,3), (2,4), (3,3), and (3,4) may be combined into one signal and input to the readout circuit 124.

From a super pixel of a position of (1,3) to a super pixel of a position of (1,n/2−1) in a super pixel array, the switching element is switched in a similar manner, and two data lines may be grouped together to output signals.

Also, to obtain a signal from a super pixel of a position of (1,n/2) in a super pixel array, while a gate signal is applied to the second gate line GL(2) and the third gate line GL(3), the (n−1)-th switching element 123-(n−1) connected to the (n−1)-th data line DL(n−1) is connected to the readout circuit 124 and the n-th switching element 123-n connected to the n-th data line DL(n) is connected to the (n−1)-th data line DL(n−1). Therefore, signals obtained from four pixels of positions of (2,n−1), (2,n), (3,n−1), and (3,n) may be combined into one signal and input to the readout circuit 124.

When signals of the second row and the third row are obtained, signals are sequentially obtained from the rest of the rows that are grouped by two.

As illustrated in FIG. 21, to obtain a signal from a super pixel of a position of (m/2−1,1) in a super pixel array, a gate signal is applied to the (m−2)-th gate line GL(m−2) and the (m−1)-th gate line GL(m−1). While the gate signal is applied, the first switching element 123-1 is turned on and the second switching element 123-2 is connected to the first data line DL(1). Therefore, signals obtained from four pixels of positions of (m−2,1), (m−2,2), (m−1,1), and (m−1,2) may be input to the readout circuit 124.

To obtain a signal from a super pixel of a position of (m/2−1,2) in a super pixel array, the third switching element 123-3 is connected to the readout circuit 124 and the fourth switching element 123-4 is connected to the third data line DL(3). Therefore, signals obtained from four pixels of positions of (m−2,3), (m−2,4), (m−1,3), and (m−1,4) may be combined into one signal and input to the readout circuit 124.

From a super pixel of a position of (m/2−1,3) to a super pixel of a position of (m/2−1,n/2−1) in a super pixel array, the switching element is switched in a similar manner, and two data lines may be grouped together to output signals.

Also, to obtain a signal from a super pixel of a position of (m/2−1,n/2) in a super pixel array, while a gate signal is applied to the (m−2)-th gate line GL(m−2) and the (m−1)-th gate line GL(m−1), the (n−1)-th switching element 123-(n−1) connected to the (n−1)-th data line DL(n−1) is connected to the readout circuit 124 and the n-th switching element 123-n connected to the n-th data line DL(n) is connected to the (n−1)-th data line DL(n−1). Therefore, signals obtained from four pixels of positions of (m−2,n−1), (m−2,n), (m−1,n−1), and (m−1,n) may be combined into one signal and input to the readout circuit 124.

In addition, a gate signal is applied to the first gate line GL(1) and the m-th gate line GL(m) and a process of obtaining a signal by grouping two data lines may be applied.

However, in the fourth imaging, signals obtained from the first gate line GL(1) and the m-th gate line GL(m) are the result of 1×2 pixel binning. Therefore, to further increase a frame rate, no gate signal may be applied to the first gate line GL(1) and the m-th gate line GL(m).

The structure of the X-ray detector 120 is not limited to the example of FIG. 13. Other structures in which the binning pattern is changed to obtain a signal may also be applied. Hereinafter, another exemplary structure of the X-ray detector 120 will be described.

Figure 22:
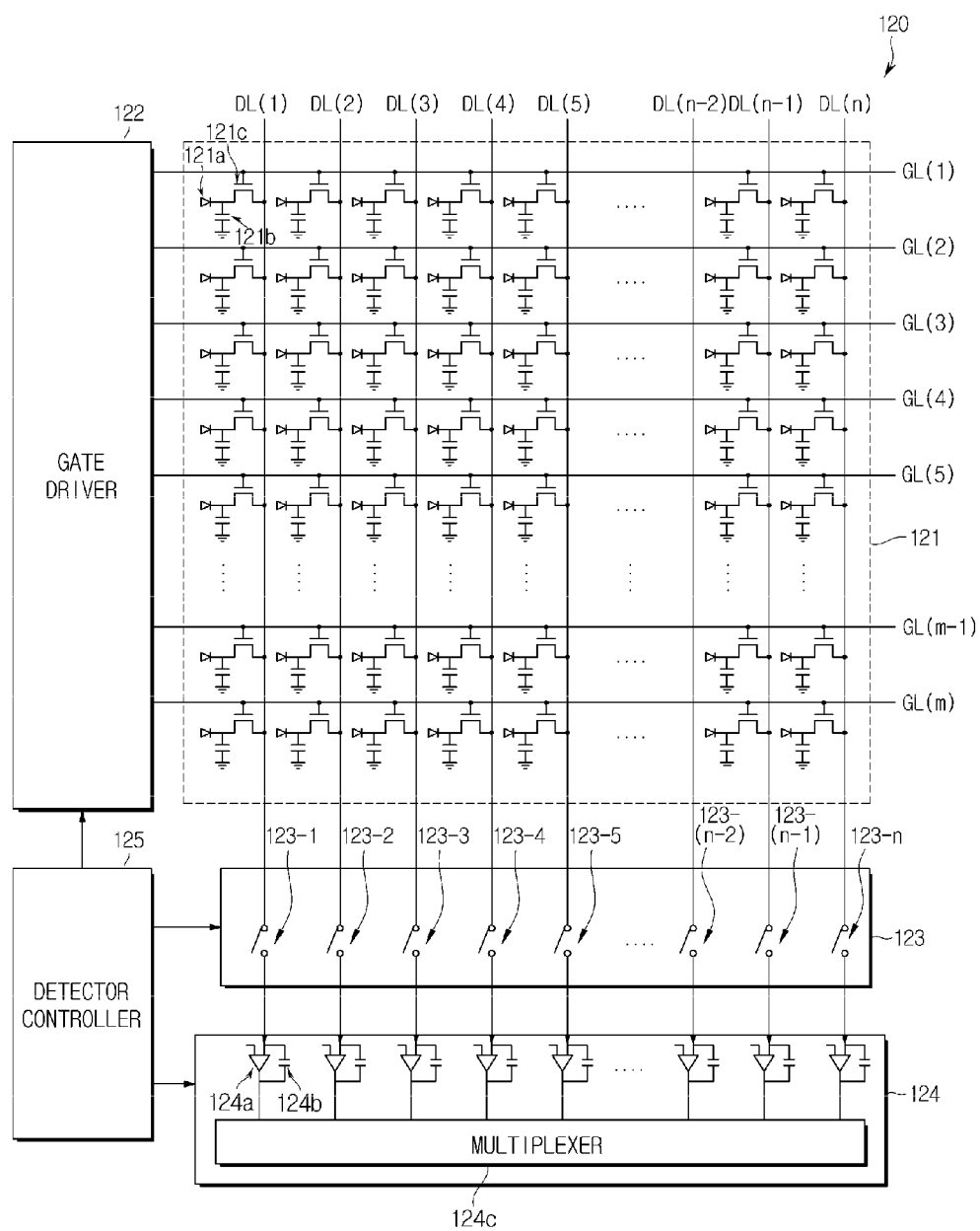
FIG. 22 is a diagram illustrating a structure of an X-ray detector according to an exemplary embodiment.
Figure 23A:
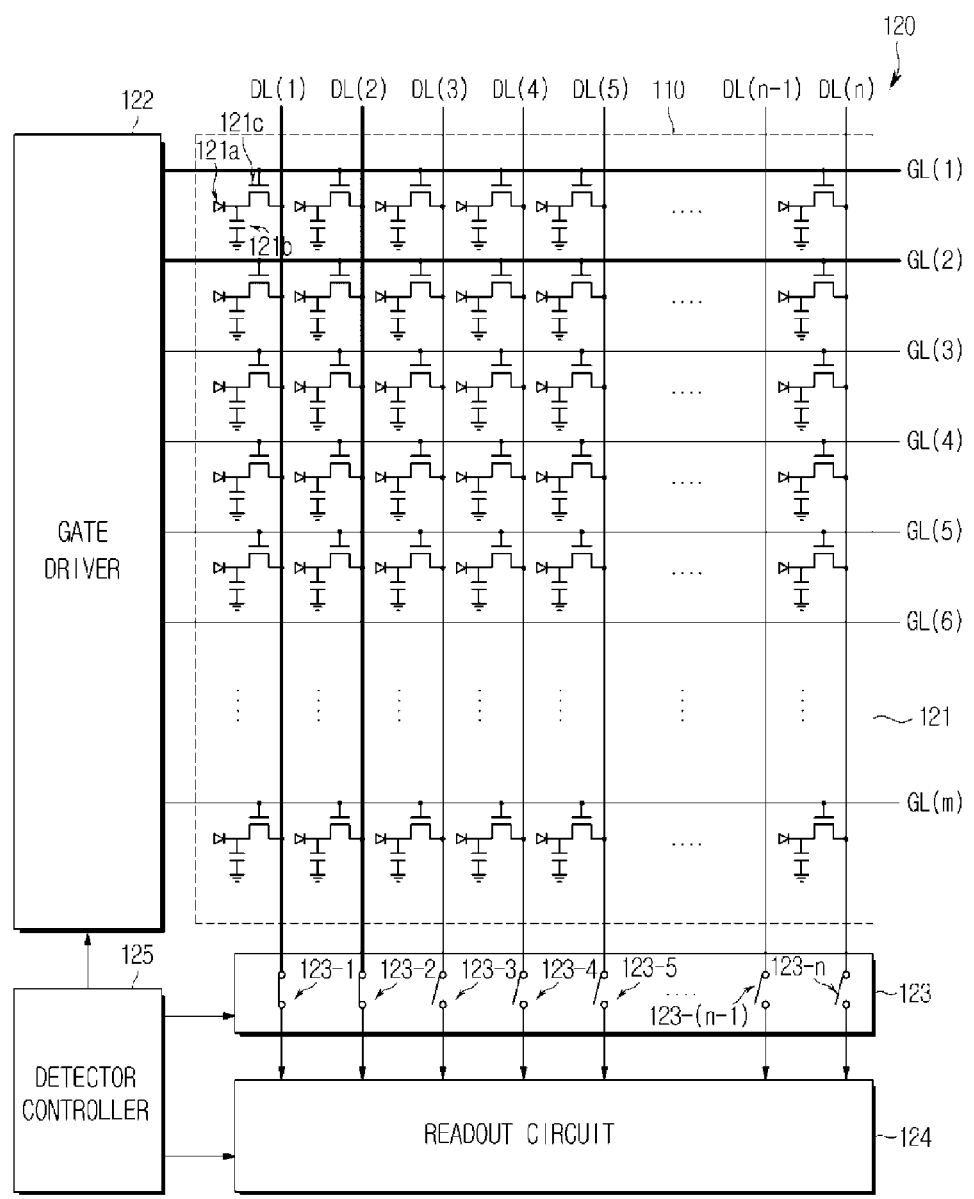
FIGS. 23A and 23B are diagrams illustrating an operation of an X-ray detector according to the exemplary embodiment of FIG. 22.
Figure 23B:
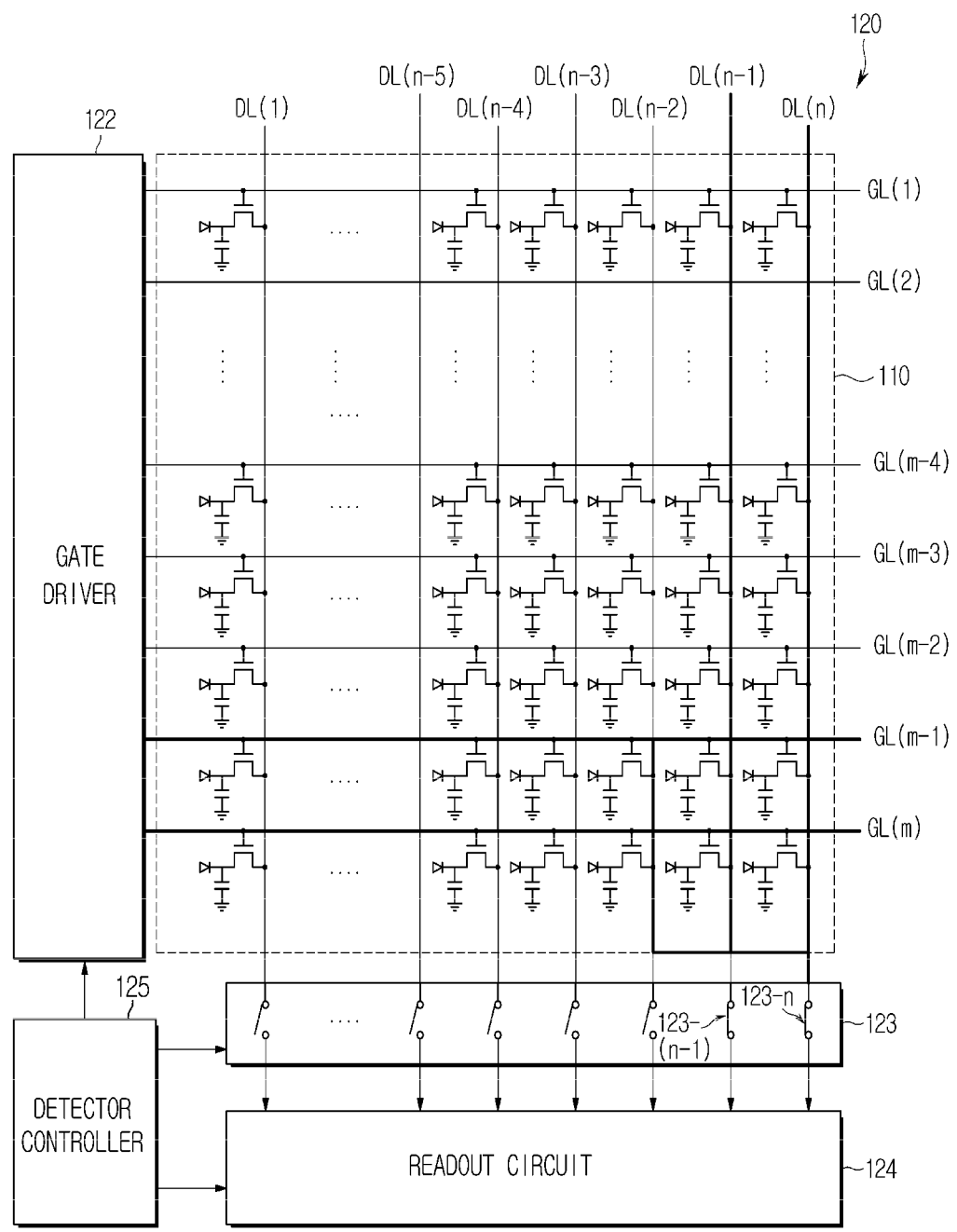

FIG. 22 is a diagram illustrating a structure of an X-ray detector according to another exemplary embodiment. FIGS. 23A and 23B are diagrams illustrating an operation of an X-ray detector according to the exemplary embodiment of FIG. 22.

As illustrated in FIG. 22, the switching elements of the switch 123 may be implemented to switch between on and off states. Hereinafter, an exemplary switching operation of the switch 123 according to the exemplary embodiment of FIG. 22 will be described using a case in which 2×2 pixel binning is applied to obtain a signal.

To receive a signal by grouping two data lines, a signal may be obtained for each pair of the data lines with a time difference between respective pairs. As illustrated in FIGS. 23A and 23B, to simultaneously obtain signals from four pixels of positions of (1,1), (1,2), (2,1), and (2,2), the first gate line GL(1) and the second gate line GL(2) may be simultaneously turned on, and the first switching element 123-1 and the second switching element 123-2 may be simultaneously turned on. Therefore, a signal may be obtained from the first data line DL(1) and the second data line DL(2).

Also, a signal is obtained from the third data line DL(3) and the fourth data line DL(4) with a time difference from the first and second data lines DL(1) and DL(2). Similarly, the (n−1)-th switching element 123-(n−1) and the n-th switching element 123-n are simultaneously turned on. Therefore, a signal may be obtained from the (n−1)-th data line DL(n−1) and the n-th data line DL(n).

A signal may be obtained from the third row to the (m−2)-th row in a similar manner.

Also, to obtain a signal from the last two rows, a gate signal is simultaneously applied to the (m−1)-th gate line GL(m−1) and the m-th gate line GL(m), and the switching element is simultaneously turned on by grouping two data lines from the first data line DL(1) to the n-th data lines DL(n). Finally, to simultaneously obtain signals from four pixels of positions of (m−1,n−1), (m−1,1), (m,n−1), and (m,n) in a super pixel array, while a gate signal is applied to the (m−1)-th gate line GL(m−1) and the m-th gate line GL(m), the (n−1)-th switching element 123-(n−1) and the n-th switching element 123-n may be simultaneously turned on.

A component for summing signals obtained from two data lines may be provided at an input terminal or an output terminal of the readout circuit 124.

In addition, in this example, the readout circuit 124 may include the amplifier 124a and the multiplexer 124c. In this case, the multiplexer 124c may be implemented as an n-to-1 MUX or implemented as an n-to-p (p is the number of columns included in a binning unit for performing pixel binning) MUX.

In the example of FIG. 22, the amplifier 124a is positioned at an input terminal of the multiplexer 124c. However, to improve a noise characteristic, the amplifier 124a may be positioned at an output terminal of the multiplexer 124c.

Also, in another exemplary embodiment, no multiplexer may be provided in the readout circuit 124, and signals obtained for each column may be output in parallel.

Figure 24:
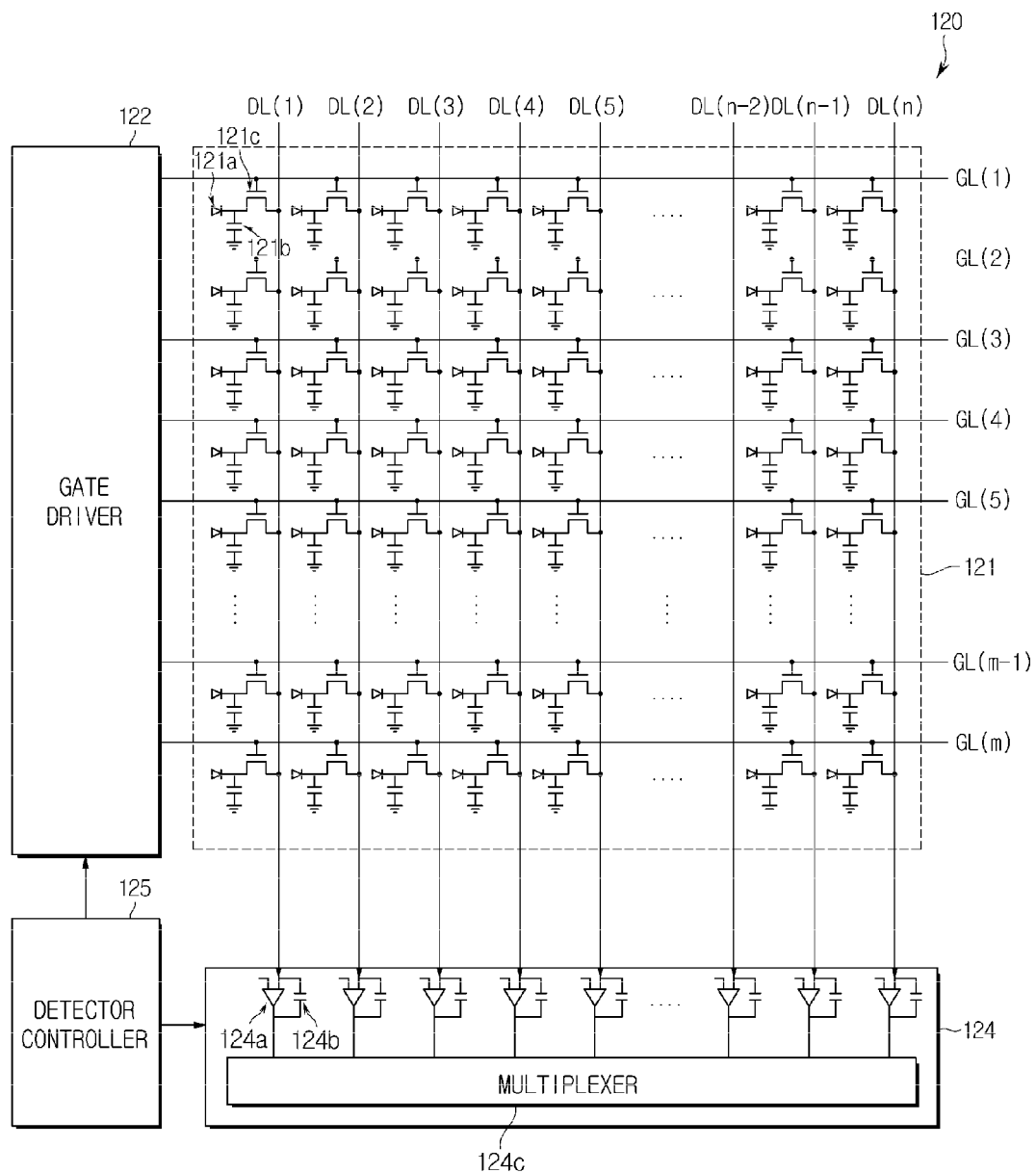
FIG. 24 is a diagram illustrating a structure of an X-ray detector according to an exemplary embodiment.

FIG. 24 is a diagram illustrating a structure of an X-ray detector according to still another exemplary embodiment.

In the X-ray detector 120 according to the exemplary embodiments described above, the switch 123 is provided between the detection area 121 and the readout circuit 124. However, according to still another example of the X-ray detector 120, as illustrated in FIG. 24, the switch 123 is not provided, and a multiplexer 124c implemented as an n-to-p (p is the number of columns included in a binning set for performing pixel binning) MUX is provided in the readout circuit 124. Therefore, it is possible to change the binning pattern. In the example of FIG. 24, it is assumed that p is two.

Specifically, when signals obtained from the first data line DL(1) to signals obtained from the n-th data line DL(n) are input to the multiplexer 124c, the multiplexer 124c simultaneously outputs signals obtained from the first data line DL(1) and signals obtained from the second data line DL(2) according to a current binning pattern, and simultaneously output signals obtained from the third data line DL(3) and signals obtained from the fourth data line DL(4) with a time difference from the output of signals from the first and second data lines DL(1) and DL(2). Similarly, signals obtained from the (n–1)-th data line DL(n–1) and signals obtained from the n-th data line DL(n) may be output together.

In this case, as illustrated in FIG. 24, the amplifier 124a may be disposed at the input terminal of the multiplexer 124c. However, the amplifier 124a may be disposed at an output terminal of the multiplexer 124c, and when signals obtained from two data lines are summed and pass through the amplifier 124a, a noise characteristic of the X-ray image may be improved.

The structure and the operation of the X-ray detector 120 according to exemplary embodiments in which the binning pattern is changed and the plurality of low-resolution X-ray images having different pieces of information on the same scene are obtained have been described above. Hereinafter, a process of reconstructing the high-resolution X-ray image using the plurality of low-resolution X-ray images will be described.

Figure 25:
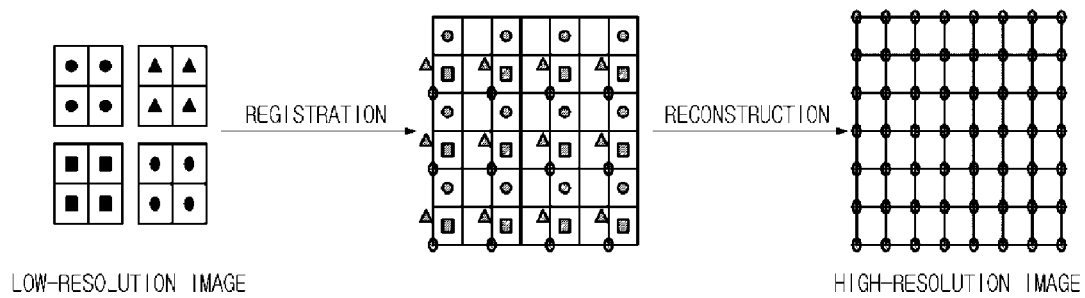
FIG. 25 is a diagram schematically illustrating a process of an image processor reconstructing a high-resolution image according to an exemplary embodiment.

FIG. 25 is a diagram schematically illustrating a process of an image processor reconstructing a high-resolution image according to an exemplary embodiment.

The image processor 130 reconstructs the high-resolution X-ray image using the plurality of low-resolution X-ray images obtained by the X-ray detector 120. For this purpose, a super high-resolution image reconstruction technique may be used.

The super high-resolution image reconstruction technique is also called a high-resolution image reconstruction technique. Also, any technique in which the plurality of low-resolution X-ray images are used to reconstruct the high-resolution X-ray image may be applied to the image processor 130.

The super high-resolution image reconstruction technique is a technique in which several low-resolution images having different pieces of information on the same scene are used to generate one high-resolution image. For example, when four low-resolution images that are horizontally or vertically shifted by one pixel or ½ pixel are obtained, these images may be summed to generate one high-resolution image.

As described above, the X-ray detector 120 may horizontally or vertically shift the binning pattern by one pixel, and the plurality of low-resolution X-ray images having different pieces of pixel information on the same scene are obtained. Therefore, the image processor 130 may reconstruct the high-resolution X-ray image using the plurality of low-resolution X-ray images obtained by the X-ray detector 120.

As illustrated in FIG. 25, to generate the high-resolution image, a registration process and a reconstruction process may be performed.

The registration process is used to obtain a geometric alignment relation among low-resolution images. For example, when the X-ray detector 120 obtains four low-resolution X-ray images that are horizontally or vertically shifted by one pixel by changing the binning pattern as described above, an alignment relation illustrated in FIG. 25 may be obtained through the registration process.

Also, a spatial domain method in which a relation between the low-resolution image and the high-resolution image is analyzed in a space domain and the low-resolution image is reconstructed as the high-resolution image based on the analysis, or a frequency domain method in which a relation between the low-resolution image and the high-resolution image is analyzed in a frequency domain and the low-resolution image is reconstructed as the high-resolution image based on the analysis may be applied, and pixel information may be mapped to a high resolution grid (HR grid).

For example, when the spatial domain method is applied, the high-resolution image may be generated through a reconstruction technique such as, for example, non-uniform interpolation, a probabilistic method, regularization, projection onto convex sets (POCS), and iterative back projection.

Also, a restoration process such as de-noising and de-blurring may be applied. In addition, a contrast and a frequency response characteristic of an image may be controlled through contrast processing, frequency processing, and the like. Quality of a diagnostic image may be improved through spatial frequency processing. Objective image enhancement may be implemented through contrast processing.

Figure 26:
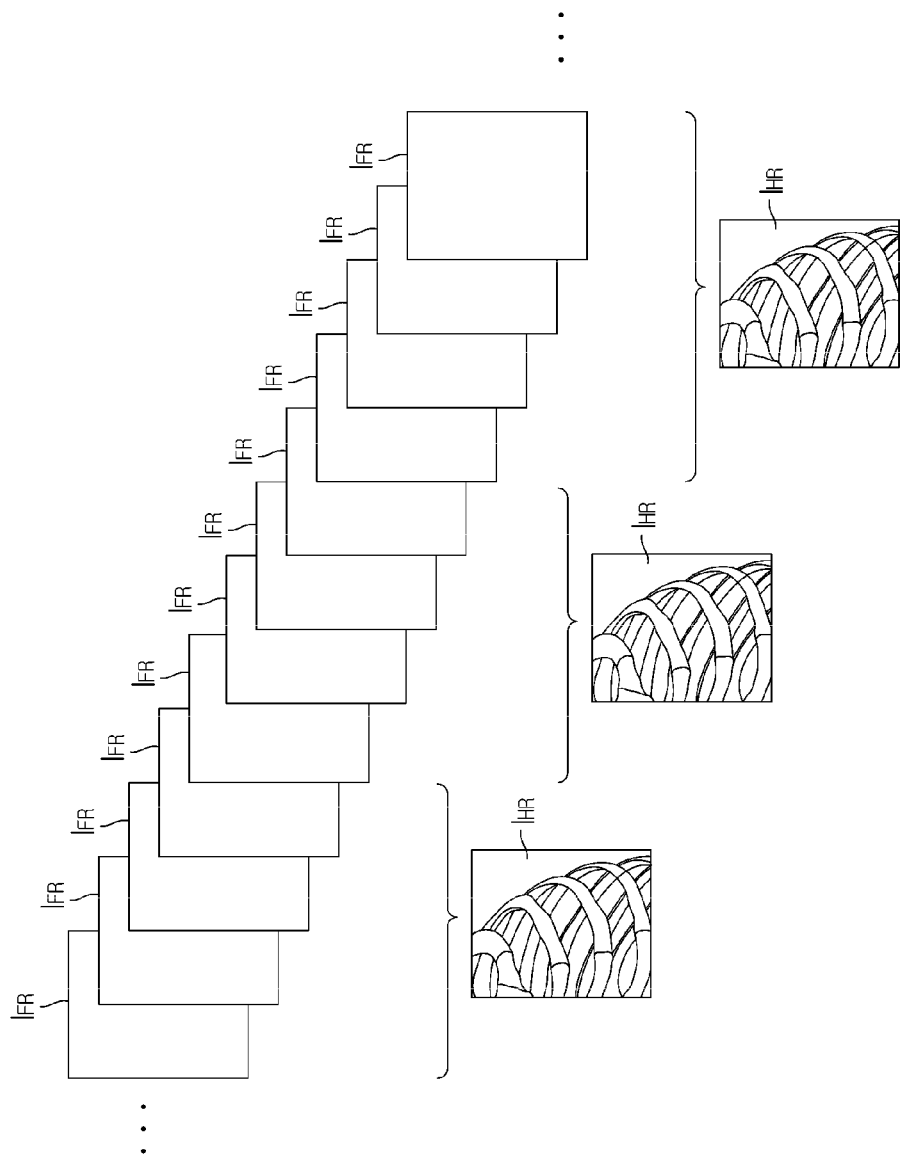
FIGS. 26 and 27 are diagrams illustrating reconstructing a high-resolution image by using low-resolution X-ray images when an X-ray imaging apparatus according to an exemplary embodiment images a video.
Figure 27:
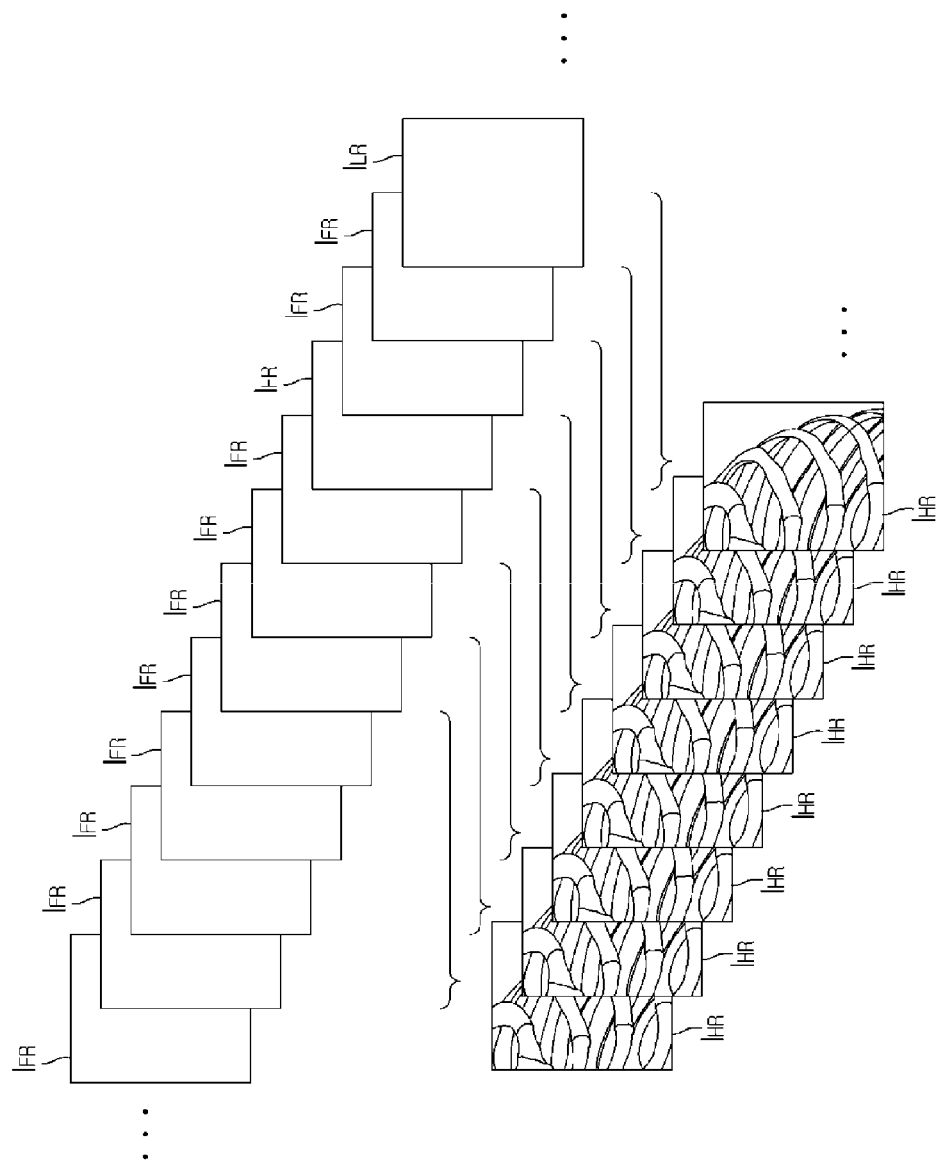

FIGS. 26 and 27 are diagrams illustrating reconstructing a high-resolution image by using low-resolution X-ray images when an X-ray imaging apparatus according to an exemplary embodiment images a video.

When the X-ray imaging apparatus 100 images a video (or a dynamic image), a set of a plurality of low-resolution frame images that are continuously obtained may be set and the high-resolution X-ray image may be reconstructed based on the set of the plurality of low-resolution frame images.

For example, as illustrated in FIG. 26, based on an input of low-resolution frame images $I_{FR}$ from the X-ray detector 120, the image processor 130 may perform high-resolution image reconstruction. That is, the image processor 130 waits until four frame images $I_{FR}$ are input, and when four frame images $I_{FR}$ are input, generates one high-resolution image $I_{HR}$ using the input frame images $I_{FR}$, and waits again until next four frame images $I_{FR}$ are input, and may generate one high-resolution image $I_{HR}$ based on the next input frame images $I_{FR}$.

In an exemplary embodiment illustrated in FIG. 27, the image processor 130 may perform high-resolution image reconstruction according to an input rate of the frame images $I_{FR}$. Specifically, the image processor 130 does not wait until four frame images $I_{FR}$ are input. Instead, the image processor 130 applies a sliding window method, shifts frame images $I_{FR}$ one by one, and may perform high-resolution image reconstruction based on the shifted frame images $I_{FR}$.

In addition, when the plurality of continuous frame images $I_{FR}$ are registered, the image processor 130 may perform motion estimation in unit of a sub-pixel. A motion estimation method includes, for example, a method in which a cross-correlation spectrum is obtained in the frequency domain through discrete Fourier transform (DFT) between images, a method in which a sub-pixel of an original image is searched for and movement information in unit of a sub-pixel is extracted, and the like.

The generated high-resolution X-ray image is displayed on the display 141 and may be used in various areas for diagnosis and procedures.

Hereinafter, an exemplary embodiment of a method of controlling an X-ray imaging apparatus will be described.

FIG. 28 is a flowchart illustrating a method of controlling an X-ray imaging apparatus according to an exemplary embodiment.

In the method of controlling an X-ray imaging apparatus according to an exemplary embodiment, the X-ray imaging apparatus 100 according to above described exemplary embodiments may be applied. Therefore, descriptions in FIGS. 1 to 27 may be applied to the method of controlling an X-ray imaging apparatus according to an exemplary embodiment.

As illustrated in FIG. 28, the binning pattern is changed and the plurality of low-resolution X-ray images are obtained (operation 310).

A size or a combination of the binning set may be determined in consideration of an image obtaining rate (or frame rate), a resolution, a characteristic of an object, and the like. Since pixel binning is performed, a dose for each X-ray image may be decreased compared to when pixel binning is not performed.

For example, while the binning pattern is horizontally or vertically moved by one pixel size, a low-resolution X-ray image may be obtained. A structure of the X-ray detector 120 in which the binning pattern can be changed may include a structure in which signals of two data lines are grouped and combined as illustrated in FIG. 13, a structure in which signals are obtained from two data lines with a time difference as illustrated in FIG. 22, or a structure in which signals are obtained at a time but the multiplexer 124b outputs the signals by grouping two signals as illustrated in FIG. 24. However, the structure of the X-ray detector 120 is not limited to the above examples. Other than the above structures, any structure capable of changing the binning pattern may be applied to the method of controlling an X-ray imaging apparatus according to exemplary embodiments.

Also, the plurality of low-resolution X-ray images are used to reconstruct the high-resolution X-ray image (operation 320).

For this purpose, the super high-resolution image reconstruction technique as described above may be used.

For example, when the X-ray detector 120 horizontally or vertically shifts the binning pattern by one pixel and the plurality of low-resolution X-ray images having different pieces of pixel information on the same scene are obtained, the image processor 130 may reconstruct the high-resolution X-ray image using the plurality of low-resolution X-ray images obtained by the X-ray detector 120.

To reconstruct the high-resolution image, the registration process and the restoration process as described above may be performed. That is, the registration process may be used to obtain a geometric alignment relation among low-resolution images. The restoration process may be used to compensate for phenomena such as distortion, noise, and blur of the low-resolution image.

Also, a spatial domain method in which a relation between the low-resolution image and the high-resolution image is analyzed in a space domain and the low-resolution image is reconstructed as the high-resolution image based on the analysis, or a frequency domain method in which a relation between the low-resolution image and the high-resolution image is analyzed in a frequency domain and the low-resolution image is reconstructed as the high-resolution image based on the analysis may be applied, and pixel information may be matched to a high resolution grid (HR grid).

For example, when the spatial domain method is applied, the high-resolution image may be reconstructed through a technique such as, for example, non-uniform interpolation, a probabilistic method, regularization, projection onto convex sets (POCS), and iterative back projection.

Also, an image processing process (or the restoration process) such as de-noising and de-blurring is applied. In addition, a contrast and a frequency response characteristic of an image may be controlled through contrast processing, frequency processing, and the like. Quality of a diagnostic image may be improved through spatial frequency processing. Objective image enhancement may be implemented through contrast processing.

When the X-ray imaging apparatus 100 images a video (or a dynamic image), a set of a plurality of low-resolution frame images that are continuously obtained may be set and the high-resolution X-ray image may be reconstructed based on the set of the plurality of low-resolution frame images.

For example, when u frame images are used to reconstruct one high-resolution X-ray image, the image processor 130 may perform high-resolution image reconstruction in response to receiving u low-resolution frame images $I_{FR}$ from the X-ray detector 120, or may perform high-resolution image reconstruction by applying a sliding window method according to an input rate of the frame image and shifting images one by one.

In addition, when the plurality of continuous frame images are registered, the image processor 130 may perform motion estimation in unit of a sub-pixel. A motion estimation method includes, for example, a method in which a cross-correlation spectrum is obtained in the frequency domain through discrete Fourier transform (DFT) between images, a method in which a sub-pixel of an original image is searched for and movement information in unit of a sub-pixel is extracted, and the like.

Also, the generated high-resolution X-ray image is displayed on the display (operation 330).

According to the X-ray imaging apparatus and the method of controlling the same according to the exemplary embodiments described above, the binning pattern is changed, the plurality of low-resolution X-ray images having different pieces of information on the same scene are obtained, and high-resolution image reconstruction is performed using the plurality of low-resolution X-ray images. Therefore, it is possible to obtain a low dose, an excellent noise characteristic, and an excellent image obtaining rate, and improve a spatial resolution.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
    an X-ray detector comprising pixels, which is configured to change a binning pattern differently applied to the pixels and obtain first resolution X-ray images corresponding to a plurality of binning patterns which are different from each other; and
    an image processor configured to generate a second resolution X-ray image using the first resolution X-ray images, the second resolution X-ray image having a higher resolution than the first resolution X-ray images.

2. The X-ray imaging apparatus according to claim 1, wherein the X-ray detector is configured to shift the binning pattern by at least one pixel in at least one of a first direction and a second direction different from the first direction.

3. The X-ray imaging apparatus according to claim 1, wherein the pixels are two dimensionally arranged in columns and rows, and configured to output signals corresponding to incident X-rays, and the X-ray detector further comprises:
    gate lines configured to connect to the pixels in a row direction;
    data lines configured to connect to the pixels in a column direction;
    a readout circuit configured to obtain the signals from the pixels through the data lines; and
    a switch configured to selectively connect the data lines and the readout circuit.

4. The X-ray imaging apparatus according to claim 3, wherein the switch comprises switching elements configured to be connected to the data lines, and
    at least one of the switching elements comprises a two-way switch.

5. The X-ray imaging apparatus according to claim 4, wherein the switching elements are configured to selectively connect P data lines to each other, among the data lines, and
    P is equal to a number of pixel columns included in one binning set.

6. The X-ray imaging apparatus according to claim 5, wherein the signals obtained from the selectively connected P data lines are combined into one signal which is input to the readout circuit,
    the switching elements are grouped into groups of P switching elements, and
    the groups of P switching elements are turned ON with a time difference.

7. The X-ray imaging apparatus according to claim 1, wherein the pixels are two dimensionally arranged in columns and rows, and configured to output signals corresponding to incident X-rays, and the X-ray detector further comprises:
    gate lines configured to connect to the pixels in a row direction;
    data lines configured to connect to the pixels in a column direction; and
    a readout circuit configured to obtain the signals from the pixels through the data lines.

8. The X-ray imaging apparatus according to claim 7, wherein the readout circuit comprises a multiplexer configured to output the signals in groups of P signals, among the signals obtained from the data lines, with a time difference,
    the readout circuit further comprises P amplifiers connected to an output terminal of the multiplexer, and
    P is equal to a number of data lines included in one binning set.

9. The X-ray imaging apparatus according to claim 1, wherein the first resolution X-ray images have different pieces of pixel information of a same portion of an object.

10. The X-ray imaging apparatus according to claim 1, wherein the image processor is configured to generate the second resolution image by using at least one of a spatial domain method and a frequency domain method.

11. The X-ray imaging apparatus according to claim 1, wherein the X-ray detector is configured to obtain a video comprising frame images, and
    the frame images comprise the first resolution X-ray images.

12. The X-ray imaging apparatus according to claim 11, wherein the image processor is configured to generate the second resolution X-ray image in response to an input of one of the frame images.

13. The X-ray imaging apparatus according to claim 11, wherein, when a predetermined number of frame images are input, the image processor is configured to generate the second resolution X-ray image using the predetermined number of frame images.

14. The X-ray imaging apparatus according to claim 1, further comprising:
    a display configured to display the second resolution X-ray image.

15. An X-ray imaging method comprising:
    changing a binning pattern differently applied to pixels of an X-ray detector and obtaining first resolution X-ray images corresponding to a plurality of binning patterns which are different from each other; and
    generating a second resolution X-ray image using the first resolution X-ray images, the second resolution X-ray image having a higher resolution than the first resolution X-ray images.

16. The method according to claim 15, wherein the changing the binning pattern comprises:
    shifting the binning pattern by at least one pixel in at least one of a first direction and a second direction different from the first direction.

17. The method according to claim 15, further comprising:
    displaying the second resolution X-ray image.

18. An X-ray detector comprising:
    a two-dimensional (2D) array of pixels arranged in columns and rows, and configured to output signals corresponding to incident X-rays;
    gate lines configured to connect to the pixels in a row direction;
    data lines configured to connect to the pixels in a column direction;
    a readout circuit configured to obtain signals from the pixels through the data lines;
    a switch configured to selectively connect the data lines and the readout circuit; and
    a detector controller configured to control the switch to vary a binning pattern differently applied to the pixels and obtain a plurality of first resolution X-ray images corresponding to a plurality of different patterns of binning.

19. The X-ray detector according to claim 18, further comprising:
a gate driver configured to apply an ON signal to the gate lines,
wherein the detector controller is configured to control the gate driver and the switch so that the gate lines and the data lines corresponding to binning pattern sets are selected.

20. The X-ray detector according to claim 18, wherein the switch comprises switching elements configured to be connected to the data lines, respectively,
the switching elements selectively connect P data lines to each other, among the data lines,
the signals obtained from the selectively connected P data lines are combined into one signal which is input to the readout circuit, and
P is a number of pixel columns included in one binning set.

* * * * *